(12) United States Patent
Peluso et al.

(10) Patent No.: US 8,993,230 B2
(45) Date of Patent: Mar. 31, 2015

(54) ASYNCHRONOUS SEQUENCING OF BIOLOGICAL POLYMERS

(75) Inventors: Paul S. Peluso, San Carlos, CA (US); John S. Eid, San Francisco, CA (US); David Rank, Pacific Grove, CA (US)

(73) Assignee: Pacific Biosciences of Californ, Inc., Menlo Park, CA (US)

( * ) Notice: Subject to any disclaimer, the term of this patent is extended or adjusted under 35 U.S.C. 154(b) by 864 days.

(21) Appl. No.: 12/328,715

(22) Filed: Dec. 4, 2008

(65) Prior Publication Data

US 2010/0143900 A1 Jun. 10, 2010

(51) Int. Cl.
*C12Q 1/68* (2006.01)

(52) U.S. Cl.
CPC .................................. *C12Q 1/6874* (2013.01)
USPC ........................................... 435/6.1; 435/6.12

(58) Field of Classification Search
CPC ........... C12Q 1/6874; C12Q 2527/113; C12Q 2527/101
USPC ................... 435/6, 91.2; 536/24.33
See application file for complete search history.

(56) References Cited

U.S. PATENT DOCUMENTS

| | | | |
|---|---|---|---|
| 5,547,839 A | 8/1996 | Dower et al. | |
| 6,255,083 B1 | 7/2001 | Williams | |
| 6,787,308 B2 | 9/2004 | Balasubramanian et al. | |
| 6,917,726 B2 | 7/2005 | Levene et al. | |
| 7,056,661 B2 | 6/2006 | Korlach et al. | |
| 7,170,050 B2 | 1/2007 | Turner et al. | |
| 7,476,503 B2 | 1/2009 | Turner et al. | |
| 7,901,889 B2 | 3/2011 | Christians et al. | |
| 2003/0207266 A1* | 11/2003 | Chen et al. ......... | 435/6 |
| 2003/0215862 A1 | 11/2003 | Parce et al. | |
| 2006/0019267 A1* | 1/2006 | Quake ............... | 435/6 |
| 2006/0292611 A1* | 12/2006 | Berka et al. ....... | 435/6 |
| 2008/0286795 A1* | 11/2008 | Kawashima et al. | 435/6 |
| 2009/0088327 A1* | 4/2009 | Rigatti et al. ..... | 506/4 |
| 2011/0009276 A1* | 1/2011 | Vermaas et al. .. | 506/7 |

FOREIGN PATENT DOCUMENTS

| | | |
|---|---|---|
| WO | 90/13666 A1 | 11/1990 |
| WO | 91/06678 A1 | 5/1991 |
| WO | 93/21340 A1 | 10/1993 |
| WO | 96/27025 A1 | 9/1996 |
| WO | 99/05315 A2 | 2/1999 |

OTHER PUBLICATIONS

Bentley et al. (Accurate whole human genome sequencing using reversible terminator chemistry, Nature, vol. 456, Nov. 6, 2008).*
Illumina Data Sheet (attached, 2010).*
Shendure et al. (Next-generation DNA sequencing, Nature Biotech., vol. 26, No. 10, Oct. 2008).*
Ronaghi et al. (Analyses of Secondary Structures in DNA by Pyrosequencing, Analytical Biochernisuy 267. 65-71 (1999)).*
Levene et al., Science 299 (5607):682-686 (2003).

* cited by examiner

*Primary Examiner* — Stephanie K Mummert
*Assistant Examiner* — Aaron Priest
(74) *Attorney, Agent, or Firm* — Deana A. Arnold

(57) ABSTRACT

The present invention provides methods, reagents and apparatus for conducting single molecule sequencing in an asynchronous manner. The subject methods and compositions are particularly useful for high throughput and multiplexed sequencing.

16 Claims, 1 Drawing Sheet

```
                         SEQUENCE LISTING

<160> NUMBER OF SEQ ID NOS: 7

<210> SEQ ID NO 1
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1
agttcccagt tacc                                                         14

<210> SEQ ID NO 2
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2
taccgataaa cgtc                                                         14

<210> SEQ ID NO 3
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3
acgtcgggat caatcg                                                       16

<210> SEQ ID NO 4
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 4
agttcccagt taccgataaa cgtcgggatc aatcg                                  35

<210> SEQ ID NO 5
<211> LENGTH: 4
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 5 tacc                                                                     4

<210> SEQ ID NO 6
<211> LENGTH: 5
<212> TYPE: DNA
<213> ORGANISM: Artificial Sequence
```

```
<220> FEATURE:
<223> OTHER INFORMATION: Description of Artificial Sequence: Synthetic
      oligonucleotide

<400> SEQUENCE: 6 acgtc                                                                      5

<210> SEQ ID NO 7
<211> LENGTH: 8
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 7 aatgcact                                                                   8
```

ASYNCHRONOUS SEQUENCING OF BIOLOGICAL POLYMERS

BACKGROUND OF THE INVENTION

The goal to elucidate the entire human genome has created an interest in technologies for rapid DNA sequencing, both for small and large scale applications. Important parameters are sequencing speed, length of sequence that can be read during a single sequencing run and the amount of nucleic acid template required. These research challenges suggest aiming to sequence the genetic information of single cells without prior amplification, and without the prior need to clone the genetic material into sequencing vectors. Large scale genome projects are currently too expensive to realistically be carried out for a large number of organisms or patients. Furthermore, as knowledge of the genetic basis for human diseases increases, there will be an increasing need for accurate, high-throughput DNA sequencing that is affordable for clinical applications.

Two traditional techniques for sequencing DNA are the dideoxy termination method of Sanger (Sanger et al., Proc. Natl. Acad. Sci. U.S.A. 74: 563-5467 (1977)) and the Maxam-Gilbert chemical degradation method (Maxam and Gilbert, Proc. Natl. Acad. Sci. U.S.A. 74: 560-564 (1977)). Both methods deliver four samples with each sample containing a family of DNA strands in which all strands terminate at the same type of nucleotide. Ultrathin slab gel electrophoresis, or more recently capillary array electrophoresis, is used to resolve the different length strands and to determine the nucleotide sequence, either by differentially tagging the strands of each sample before electrophoresis to indicate the terminal nucleotide, or by running the samples in different lanes of the gel or in different capillaries. Both the Sanger and the Maxam-Gilbert methods are labor- and time-intensive, and require extensive pretreatment of the DNA source. Attempts have been made to use mass spectroscopy to replace the time-intensive electrophoresis step. For a review of existing sequencing technologies, see Cheng, "High-Speed DNA-Sequence Analysis," Prog. Biochem. Biophys. 22: 223-227 (1995).

Related methods using dyes or fluorescent labels associated with the terminal nucleotide have been developed, where sequence determination is also made by gel electrophoresis and automated fluorescent detectors. For example, the Sanger-extension method has recently been modified for use in an automated microsequencing system which requires only sub-microliter volumes of reagents and dye-labeled dideoxyribonucleotide triphosphates. In U.S. Pat. No. 5,846,727 to Soper et al. ("Soper"), fluorescence detection is performed on-chip with one single-mode optical fiber carrying the excitation light to the capillary channel, and a second single-mode optical fiber collecting the fluorescent photons. Sequence reads are estimated in the range of 400-500 bases which is not a significant improvement over the amount of sequence information obtained with traditional Sanger or Maxam-Gilbert methods. Furthermore, the Soper method requires PCR amplification of template DNA, and purification and gel electrophoresis of the oligonucleotide sequencing 'ladders,' prior to initiation of the separation reaction. These systems all require significant quantities of target DNA. Other conventional methods also suffer from the same drawback. See U.S. Pat. No. 5,302,509 to Cheeseman.

In a recent improvement of a sequencing-by-synthesis methodology originally devised ten years ago, DNA sequences are being deduced by measuring pyrophosphate release upon testing DNA/polymerase complexes with each deoxyribonucleotide triphosphate (dNTP) separately and sequentially. See Ronaghi et al. ("Ronaghi"), "A Sequencing Method Based on Real-Time Pyrophosphate," Science 281: 363-365 (1998); and Hyman, "A New Method of Sequencing DNA," Anal. Biochem. 174: 423-436 (1988). While using native nucleotides, the method requires synchronization of polymerases on the DNA strands which greatly restricts sequence read lengths. Only about 40 nucleotide reads were achieved, and it is not expected that the detection method can approach single molecule sensitivity due to limited quantum efficiency of light production by luciferase in the procedure presented by Ronaghi. Further, overall sequencing speed is limited by washing steps, subsequent chemical steps in order to identify pyrophosphate presence, and the time required to test each base pair to be sequenced with all of the four bases sequentially. Additionally, difficulties in accurately determining homonucleotide stretches in the sequences have been recognized.

Previous, generally unsuccessful (albeit seminal) attempts at single molecule sequencing have utilized exonucleases to sequentially release individual fluorescently-labeled bases as a second step after DNA polymerase has formed a complete complementary strand. See Goodwin et al., "Application of Single Molecule Detection to DNA Sequencing," Nucleos. Nucleot. 16: 543-550 (1997). It consists of synthesizing a DNA strand labeled with four different fluorescent dNTP analogs, subsequent degradation of the labeled strand by the action of an exonuclease, and detection of the individual released bases in a hydrodynamic flow detector. However, both polymerase and exonuclease have to show activity on a highly modified DNA strand, and the generation of a DNA strand substituted with four different fluorescent dNTP analogs has not yet been achieved. See Dapprich et al., "DNA Attachment to Optically Trapped Beads in Microstructures Monitored by Bead Displacement," Bioimaging 6: 25-32 (1998). Furthermore, little information is known about the relationship between the degree of labeling of DNA and inhibition of exonuclease activity. See Dorre et al., "Techniques for Single Molecule Sequencing," Bioimaging 5: 139-152 (1997).

In a second approach utilizing exonucleases, native DNA is digested while it is being pulled through a thin liquid film in order to spatially separate cleaved nucleotides. See Dapprich et al., "DNA Attachment to Optically Trapped Beads in Microstructures Monitored by Bead Displacement," Bioimaging 6: 25-32 (1998). They then diffuse a short distance before becoming immobilized on a surface for detection. However, most exonucleases exhibit sequence and structure-dependent cleavage rates, resulting in difficulties in data analysis and matching sets from partial sequences.

Regardless of the detection system, methods which utilize exonucleases have not been developed into methods that meet today's demand for rapid, high-throughput sequencing. In addition, most exonucleases have relatively slow turnover rates, and the proposed methods require extensive pretreatment, labeling and subsequent immobilization of the template DNA on the bead in the flowing stream of fluid, all of which make a realization into a simple high-throughput system more complicated.

Other, more direct approaches to DNA sequencing have been attempted, such as determining the spatial sequence of fixed and stretched DNA molecules by scanned atomic probe microscopy. Problems encountered with using these methods include the narrow spacing of the bases in the DNA molecule (only about 0.34 nm) and the small physicochemical differences to be recognized by these methods. See Hansma et al., "Reproducible Imaging and Dissection of Plasmid DNA Under Liquid with the Atomic Force Microscope," Science 256: 1180-1184 (1992).

In a recent approach for microsequencing using polymerase, but not exonuclease, a set of identical single stranded DNA (ssDNA) molecules were linked to a substrate and the sequence was determined by repeating a series of reactions using fluorescently labelled dNTPs. See U.S. Pat. No. 5,302,509 to Cheeseman. However, this method requires that each base be added with a fluorescent label and 3'-dNTP blocking groups. After the base is added and detected, the fluorescent label and the blocking group are removed and the next base is added to the polymer.

Optical methods and devices for sequencing biological polymers have several limitations. One limitation is that the lifetime of a polymerization enzyme has an inverse relationship with respect to the time the polymerization enzyme is illuminated. That is, once a polymerization enzyme is illuminated to begin sequencing a biological polymer, the polymerization enzyme loses its activity (and functionality) after a certain time period, which is typically less than the time period required to sequence the entire biological polymer with a single polymerization enzyme. One solution is to divide a biological polymer into smaller subunits, with the number of subunits selected such that each subunit can be sequenced before the polymerization enzyme associated with that subunit loses its functionality. However, this process is time consuming and costly, and prone to error. Another limitation of the conventional sequencing methods is that they are typically slow. Obtaining accurate sequencing information can take long periods of time, up to several days.

The human genome project has intensified the need for rapid, small and large-scale DNA sequencing methods that will allow high throughput with minimal starting material. Accordingly, there is a need for sequencing methods with improved throughput and accuracy.

SUMMARY OF THE INVENTION

In one aspect of the invention, a method for sequencing a target nucleic acid molecule is provided. The method comprises providing a first nucleic acid molecule and a second nucleic acid molecule, the first nucleic acid molecule and the second nucleic acid molecule having the same or essentially the same sequences as the target nucleic acid molecule, wherein the first nucleic acid molecule is complexed with a first primer and a first polymerase and the second nucleic acid molecule is complexed with a second primer and a second polymerase. The first nucleic acid molecule is subjected to a first polymerization reaction to yield a first strand complementary to the first nucleic acid molecule. The second nucleic acid molecule is subjected to a second polymerization reaction to yield a second strand complementary to the second nucleic acid molecule. Asynchronous polymerization reactions between the first nucleic acid molecule and the second nucleic acid molecule are established. Time sequences of incorporation of nucleotides or nucleotide analogs into the first strand and the second strand during the asynchronous polymerization reactions are obtained, which are compiled to sequence the target nucleic acid molecule. The sequences can be compiled through consensus.

In another aspect of the invention, a method for sequencing a target nucleic acid molecule comprises providing two or more nucleic acid molecules having the same or essentially the same sequences as the target nucleic acid molecule, wherein each of the two or more nucleic acid molecules is complexed with a primer and a polymerase, wherein individual polymerases are complexed at different locations of the target nucleic acid molecule such that two or more nascent strands of different but overlapping sequences are achieved. The two or more nucleic acid molecules are subjected to a polymerization reaction to yield the two or more nascent strands. Time sequences of incorporation of nucleotides or nucleotide analogs into individual nascent stands during the polymerization reaction are obtained, which are compiled to sequence the target nucleic acid molecule.

In yet another aspect of the invention, a method for sequencing a target nucleic acid molecule comprises providing two or more nucleic acid molecules having the same or essentially the same sequences as the target nucleic acid molecule, wherein each of the two or more nucleic acid molecules is complexed with a primer and a polymerase. The two or more nucleic acid molecules are subjected to polymerization reactions to yield two or more nascent strands of different but overlapping sequences. The two or more nucleic acid molecules are exposed to light for an exposure time that is less than a length of time required to form a strand complementary to the target nucleic acid molecule using the polymerase, the strand and the target nucleic acid molecule having the same or essentially the same number of nucleotides. Time sequences of incorporation of nucleotides or nucleotide analogs into individual nascent strands during the polymerization reactions are obtained, which are compiled to sequence the target nucleic acid molecule. This process can be repeated over time to obtain a time sequences of incorporation that overlaps with a previously obtained time sequence of incorporation.

In still another aspect of the invention, an apparatus for sequencing a target nucleic acid molecule is provided. The apparatus comprises an array of optical confinements for sequencing nucleic acid molecules, the optical confinements comprising target nucleic acid molecules. The apparatus further comprises a computer system configured to compile time sequences of incorporation of nucleotides or nucleotide analogs during asynchronous polymerization of two or more nucleic acid strands having different but overlapping sequences complementary to each of the target nucleic acid molecules.

INCORPORATION BY REFERENCE

All publications and patent applications mentioned in this specification are herein incorporated by reference to the same extent as if each individual publication or patent application was specifically and individually indicated to be incorporated by reference.

BRIEF DESCRIPTION OF THE DRAWINGS

The features and advantages of the invention may be further explained by reference to the following detailed description and accompanying drawings that sets forth illustrative embodiments.

DETAILED DESCRIPTION OF THE INVENTION

Figure 1A:
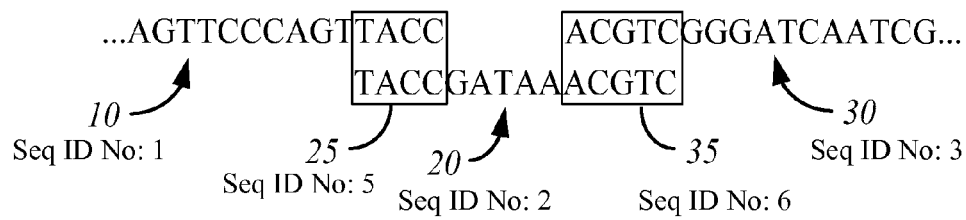
FIGS. 1A and 1B schematically illustrate a computer-assisted method for combining three nascent strand sequences (10 (SEQ ID NO: 1), 20 (SEQ ID NO: 2), and 30 (SEQ ID NO: 3)) into a target sequence (40) (SEQ ID NO: 4).

While various embodiments of the invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention.

Asynchronous sequencing can be used to obtain sequence information of a biological polymer. In some embodiments of the invention, asynchronous sequencing can be used to obtain sequence information of a biological polymer in an efficient and/or rapid manner. In some embodiments of the invention, asynchronous sequencing can comprise asynchronous polymerization reactions between enzymes polymerizing different portions of a biological polymer. The asynchronous polymerization reactions can be used to obtain different but overlapping sequences.

Methods, devices, apparatuses and compositions described herein can mitigate issues associated with the degradation of polymerization enzymes upon illumination. This is due at least in part to a polymerization enzyme polymerizing only a portion of a target nucleic acid molecule when the polymerization enzyme is illuminated to obtain sequence information.

The inventions provide for methods, compositions, and apparatuses for sequencing biological polymers in real time. The methods of the invention can comprise establishing asynchronous polymerization reactions, obtaining sequence information and compiling sequence information. The compositions of the invention can include types of biological polymers that can be sequenced and reagents that can be used in polymerization reactions. The apparatuses of the invention can comprise components for setting up polymerization reactions, obtaining sequence information and compiling sequence information.

Biological polymers can include, without limitation, double-stranded or single-stranded, linear or circular nucleic acids (e.g., DNA, circular DNA, RNA), single-stranded DNA hairpins, DNA/RNA hybrids, RNA with a recognition site for binding of the polymerase, or RNA hairpins. Methods of the invention may be suitable for sequencing complex nucleic acid structures, such as 5' or 3' non-translation sequences, tandem repeats, exons or introns, chromosomal segments, whole chromosomes, or genomes.

Asynchronous Sequencing Methods

In some embodiments of the invention, at least two nucleic acid molecules are provided. The at least two nucleic acid molecules can have identical, essentially identical, or similar sequences to a target nucleic acid molecule.

Sequence information can be obtained when a first polymerization enzyme associated with a first nucleic acid molecule and a second polymerization enzyme associated with a second nucleic acid molecule are asynchronously polymerizing strands complementary to the first and second nucleic acid molecules. The strands of nucleic acids being polymerized by the first and second polymerase can comprise overlapping and non-overlapping nucleic acid sequences. The strands of nucleic acids being polymerized (also "nascent strand" or "strand" herein) by polymerases can overlap by 5 or more nucleotides, or by 10 or more nucleotides, or by 20 or more nucleotides. Asynchronous polymerization reactions can be established using methods that utilize variations in rates of polymerization and/or localization of polymerases. A first and second polymerase can be localized at different locations on a first and second template using different primers, blocking primers, different times for initiating polymerization reactions, stochastic variations in rates of polymerization by the first and second polymerase, staggered times for collection of sequence information, or any other methods known to those skilled in the arts.

In one embodiment of the invention, asynchronous polymerization is established when the first and second polymerization enzymes have different rates of polymerization. This can be achieved when the first and second polymerization enzymes begin polymerizing strands at the same location or at different locations with respect to the target nucleic acid molecule. In another embodiment of the invention, asynchronous polymerization is established when the first and second polymerization enzymes are polymerizing different but overlapping strands, each strand being complementary to a first or second nucleic acid molecule. In yet another embodiment of the invention, asynchronous polymerization is established when the first and second polymerization enzymes are polymerizing different but overlapping strands at different rates of polymerization.

The different rates of polymerization can be a result of stochastic variation or inherent differences between the first and second polymerization enzyme. In other embodiments of the invention, the first and second polymerization reactions can have different rates of polymerization due to variations in polymerization conditions and reagents. Polymerization conditions can include temperature and pressure. Polymerization reagents can include salts, cations, energy sources, nucleotides, primers and templates.

Asynchronous polymerization reactions can be established by using a first polymerase and a second polymerase, wherein a first portion of a first template is sequenced using the first polymerase and a second portion of a second template is sequenced using the second polymerase. The first portion and the second portion can comprise the same or different nucleic acid sequences. The first and second polymerase can begin polymerizing stands complementary to the first and second template at the same or different locations on the first and second template. The locations can be determined by nucleic acid sequences on the first and second templates.

The first and second polymerase can initiate a first and second polymerization reaction, respectively, at different locations using primers with different sequences. Localization of the polymerases to different locations on a first and second template can allow for asynchronous sequence information to be obtained.

In some embodiments of the invention, asynchronous polymerization reactions can be established using the same primers and polymerization enzymes that have different rates of polymerization. Different rates of polymerization can be due to stochastic variations in rates of polymerization. In some embodiments of the invention, the first and second polymerase can initiate a first and a second polymerization reaction at the same locations using primers with the same, essentially the same or similar sequences to initiate the first and second polymerization reactions.

In one embodiment, a first and a second polymerase can be localized at different locations on a first and a second template, respectively, using blocking primers. The first polymerase can be localized at a first position on first template using a first initiating primer. The second polymerase can be localized at a second position on a second template using a second initiating primer. The first and second initiating primers can have the same, essentially the same or similar sequences. The first position and second position can be the same, essentially the same, or similar. In one embodiment, the first position and second position have the same or essentially the same sequences. The first and second polymerases can be non-strand displacing polymerases. A first blocking primer can be hybridized to the first template at a location downstream of the first position. A second blocking primer can be hybridized to the second template at a location downstream of the second position. Alternatively, the first position and second position can be different. In one embodiment, the first position and second position have different sequences.

The first and second polymerases can polymerize strands complementary to the first and second templates until the first and second polymerase are halted (and polymerization reactions are halted) by the blocking primers that have been hybridized at different locations of the first template and second template. After the first and second polymerase are halted by the first and second blocking primers and are thus disposed at different locations on the first template and second template, the first and second blocking primers can be released from the first and second template. The first and second blocking primers can be released by a change in reaction conditions, such as light, temperature or pressure, or by addition or removal of a reagent. In some cases, the blocking primers can be photoactivatable or photo-sensitive. A first set of photoactivatable or photo-sensitive primers can be sensitive to light at a first wavelength and a second set of photoactivatable or photo-sensitive primers can be sensitive to light at a second wavelength. After removal of the blocking primers, the first and second polymerases can continue polymerizing strands of nucleic acids complementary to the first and second template and be utilized to obtain asynchronous sequence information. Disposing the first and second polymerases at different or specific locations on the first and second template can establish a desired degree of relative displacement or asynchronization. Alternatively, the first and second polymerases can be disposed at the same location on the first and second template to establish synchronization. These methods can be used to maintain sufficient overlap for contiguous sequence assembly.

In some embodiments of the invention, the first polymerase and second polymerase can be initiated at different times, allowing for staggered starts for the first and second polymerases. The first polymerase can be initially localized at the first template using a first initiating primer that is essentially the same as a second initiating primer to localize the second polymerase at the second template. The time of initiation for the first and second polymerase can be controlled by the addition of a reagent or a change in an environmental (or reaction) condition. In some embodiments of the invention, the staggered starts can be established using blocking primers and staggered release of blocking primers. The blocking primer can be any blocking primer described herein. Staggered initiation times for the first and second polymerase can be used to localize the first and second polymerases to different portions of the first and second template, and therefore to establish asynchronous polymerization reactions.

In one embodiment, a first polymerase is provided at a first position of a first nucleic acid molecule and a second polymerase is provided at a second position at a second nucleic acid molecule. The first position and second position are characterized by a sequence of nucleotides or nucleotide analogs, wherein the sequence is the same. Next, reaction reagents are directed to the first polymerase to begin polymerization of a strand complementary to a portion of the first nucleic acid molecule. After a predetermined time period, reagents are directed to the second polymerase to begin polymerization of a strand complementary to a portion of the second nucleic acid molecule.

In other embodiments of the invention, the first and second polymerase can be initiated at the same time and at the same location or different locations of nucleic acid molecules they are associated with, and asynchronous polymerization can be established via stochastic variations in rates of polymerization. In one embodiment, after a predetermined time is allotted to enable the first polymerase and the second polymerase to polymerize at different rates, sequence information is obtained by, e.g., illuminating the nucleic acid molecules (see below). Stochastic variations in rates of polymerization can be established, amplified or diminished by intrinsic differences in the first and second polymerase, or by extrinsic factors, such as reaction conditions (e.g., temperature, pressure).

In some embodiments of the invention, polymerization by the first and second polymerase can be initiated at the same time. A predetermined time period is allotted to enable the first and second polymerase to polymerize asynchronously with respect to one another. With the first and second polymerase polymerizing asynchronously with respect to one another, sequence information can be obtained. A first sequence information can be obtained from the first polymerization reaction and a second sequence information to be obtained from the second polymerization. The first sequence information and second sequence information are different, but comprise nucleic acid sequences that overlap.

In embodiments of the invention, the predetermined time period allotted to enable the first and second polymerase to polymerize asynchronously with respect to one another can be 1 or more seconds, or 5 or more seconds, or 10 or more seconds, or 30 or more seconds, or 1 or more minutes, or 5 or more minutes, or 10 or more minutes, or 30 or more minutes, or 1 or more hours, or 2 or more hours.

The difference in time between the point at which polymerization is commenced and the point at which the optical confinements are illuminated can be referred to as a "hold time." The hold time can be greater than about 1 second, or greater than about 5 seconds, or greater than about 10 seconds, or greater than about 30 seconds, or greater than about 1 minute, or greater than about 5 minute, or greater than about 30 minutes, or greater than about 1 hour, or greater than about 2 hours. In one embodiment, substantially similar primers are complexed with the nucleic acid molecules and the polymerization reactions commence at substantially similar locations. Sequencing can proceed after a predetermined hold time.

Data Collection

In embodiments, having established asynchronous polymerization between two or more polymerization enzyme, sequencing information is obtained. In one embodiment, sequence information is obtained upon illumination of optical confinements having the polymerization enzymes and the nucleic acid molecules they are associated with.

During data collection (also "sequencing" herein), the length of time in which a polymerization enzyme is illuminated can be referred to as an "illumination time." In one embodiment, the illumination time is less than the length of time required for a polymerization enzyme to sequence an entire nucleic acid molecule it is associated with. For example, if a polymerization enzyme polymerizes a strand complementary to an entire nucleic acid molecule in about 1 hour, during the time period in which sequence information is collected, the polymerization enzyme is illuminated for about 5 minutes. In embodiments of the invention, during sequencing, optical confinements are illuminated for at least 30 seconds, or at least 1 minute, or at least 5 minutes, or at least 10 minutes, or at least 30 minutes, or at least 1 hour, or at least 2 hours.

In embodiments of the invention, the temporal order of base additions during the polymerization reaction is identified on a single nucleic acid molecule. Such identifying step takes place while the template-directed extension of primer or polymerization is taking place within each optical confinement. In an embodiment of the invention, single-molecule sequencing is performed in a homogenous assay that does not require transfer, separation, or washing away of any reactant or reaction by-product (e.g., fluorophore cleaved from a nucleotide) after each base addition. In certain embodiments, single-molecule sequencing is performed without adding reactants to the mixture prior to reading the next base sequence. In such an assay, stepwise addition of nucleotides (or nucleotide analogs) or removal of by-products after each base addition event is not necessary, as diffusion of reactants from a large volume of reagents above the confinement will not interfere with the detection of incorporation of nucleotides or nucleotide analogs.

In embodiments of the invention, sequence information is generated continuously as polymerases continually incorporate the appropriate nucleotides or nucleotide analogs into nascent nucleic acid strands. For a detailed discussion of such single molecule sequencing, see, e.g., Published U.S. Patent Application No. 2003/0044781, which is incorporated herein by reference in its entirety and for all purposes, and M. J. Levene, J. Korlach, S. W. Turner, M. Foquet, H. G. Craighead, W. W. Webb, "Zero-Mode Waveguides for Single-Molecule Analysis at High Concentrations," SCIENCE 299:682-686, January 2003, which is incorporated herein by reference in its entirety. In embodiments of the invention, single molecules are observed separately. This method also allows the use of target nucleic acid molecules taken directly from a biological sample, minimizing, if not eliminating, the need for cloning, sub-cloning and amplification of the target nucleic acid molecule before sequencing. This advantageously provides for rapid sequencing, at costs reduced relative to conventional methods.

In an embodiment, a polymerase enzyme is immobilized (or anchored) within the effective observation volume of an optical confinement or optical confinement area. Template dependent synthesis of a complementary strand is then carried out while observing the volume and using labeled nucleotides or nucleotide analogs that are capable of being sequentially incorporated into the nascent (and growing) nucleic acid strand without interruption (e.g., without interruption due to deprotection). In preferred methods, nucleotide analogs bearing a label on a non-incorporated phosphate group or derivative phosphate (e.g., the beta, gamma, or delta phosphate) of a nucleotide polyphosphate, which is cleaved from the analog during incorporation, are used. Such nucleotide analogs provide an advantage of being sequentially incorporated into the growing nucleic acid strand and having their labeling groups removed in the incorporation process so as to provide improved a signal-to-noise ratio during synthesis when compared to the signal-to-noise ratio that would result if such labels remained associated with the nascent strand. Further, because the incorporation event provides for prolonged presence of the labeled analogs within the observation volume (as compared to random diffusion of non-incorporated analogs into the observation volume), the signal associated with incorporation is readily identifiable.

Methods of the present invention provide for redundancy in numerous ways so as to correct for any errors that may arise in template-dependant synthesis by the polymerase enzyme. For example, because the methods of the invention focus on single molecules, redundant processes can be employed to assure that error, e.g. those of a random or non-systematic nature or those caused by mis-incorporation events by a polymerase (also "polymerization enzyme" herein), is accounted for (and corrected) during data analysis.

In embodiments, such redundancy can be supplied by utilizing arrays of multiple confinements that are being applied to a given sequence of interest. In one embodiment, sequencing may be accomplished by providing nucleic acid molecules having a sequence segment of interest in a circular template format, so that the polymerase enzymes process around the circular templates. Methods of circularization of nucleic acid segments are known to those of ordinary skill in the art, and are readily applied to template sequences in accordance with the invention. In another embodiment, sequencing may be accomplished by providing the sequence segment of interest in a linear format. In other embodiments, circularizing a linear, multi-copy template, and iteratively sequencing multiple copies multiple times can provide redundancy.

In other embodiments, a similar result is obtained by performing concatemerization of amplicons generated in a single-molecule amplification strategy, several of which are known to those skilled in the art. These strategies can employ dilution at the single molecule level, or isolation of molecules in small micelles in a two-phase emulsion during amplification. The concatamerized strand is then sequenced as a single template, and redundant information is generated from a single molecule in this fashion.

In yet another aspect, a similar result is obtained by using a long double stranded template with nicks and/or gaps at multiple locations along it. The molecule can then be caused to initiate single molecule sequencing at several locations along the strand, each location disposed in a confinement that independently sequences the strand. Because the several confinements are acting on the same template nucleic acid molecule, the result is that the same template is sequenced several times providing overlapping and/or redundant information with respect to a single molecule.

Synthesis of Sequence Information

In embodiments, sequence information from at least two nascent (or growing) strands can overlap to a certain degree. In embodiments of the invention, the monomer sequences (also "sequences" herein) of the at least two nascent strands can overlap by 5 or more monomers, or 10 or more monomers, or 20 or more monomers. In certain embodiments, sequences of nucleotides of nascent nucleic acid strands can overlap by 5 or more bases, or 10 or more bases, or 20 or more bases. A target biological polymer (e.g., target nucleic acid molecule) is sequenced by aligning overlapping (or common) sequence data from the at least two nascent strands.

Figure 2A:
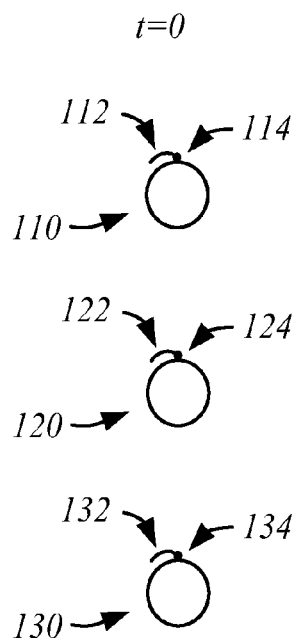
FIGS. 2A and 2B schematically illustrate a method for establishing asynchronous polymerization between three polymerization reactions.
Figure 2B:
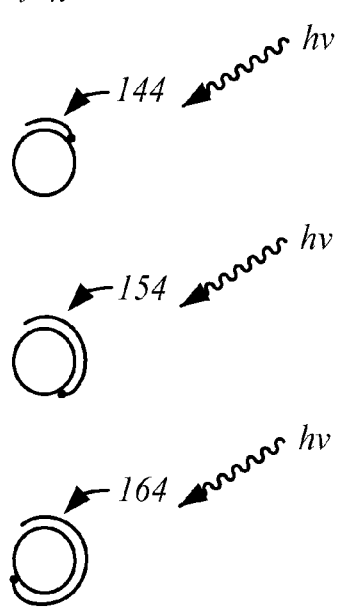

FIG. 1A shows sequence data collected by a computer system from an exemplary polymerization reaction, such as the polymerization reaction illustrated in FIG. 2B. Sequence data during polymerization of three nascent strands is collected and processed by a computer system configured to compile sequence information using overlapping sequences of individual nascent strand sequences.

With reference to FIG. 1A, a first nascent strand sequence 10 (SEQ ID NO: 1) corresponds to at least a portion of a sequence of a first nascent strand; a second nascent strand sequence 20 (SEQ ID NO: 2) corresponds to at least a portion of a sequence of a second nascent strand; and a third nascent strand sequence 30 (SEQ ID NO: 3) corresponds to at least a portion of a sequence of a third nascent strand. The first nascent strand sequence 10 (SEQ ID NO: 1) and the second nascent strand sequence 20 (SEQ ID NO: 2) have a first overlapping sequence 25. The second nascent strand sequence 20 (SEQ ID NO: 2) and the third nascent strand sequence 30 (SEQ ID NO: 3) have a second overlapping sequence 35.

Figure 1B:
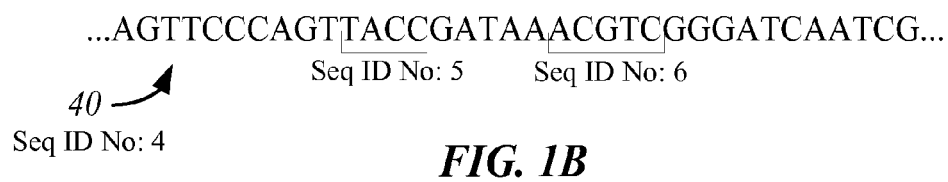

With reference to FIG. 1B, the computer system forms the template sequence 40 (SEQ ID NO: 4) by combining the first nascent strand sequence 10 (SEQ ID NO: 1), the second nascent strand sequence 20 (SEQ ID NO: 2) and the third nascent strand sequence 30 using the first overlapping sequence 25 (SEQ ID NO: 5) and the second overlapping sequence 35 (SEQ ID NO: 6). Horizontal brackets represent the respective areas of overlap of the nascent strand sequences 10 (SEQ ID NO: 1), 20 (SEQ ID NO: 2) and 30 (SEQ ID NO: 3).

While the template sequence 40 (SEQ ID NO: 4) comprises the illustrated number of nucleotides, it will be appreciated that the template sequence 40 (SEQ ID NO: 4) can comprise 50 or more, or 100 or more, or 500 or more, or 1000 or more, or 5000 or more nucleotides. As such, a relatively large number of nascent strand sequences can be combined to yield a template sequence. For example, 50 nascent strand sequences collected during the polymerization of 50 strands can be combined to sequence a nucleic acid molecule having 1000 nucleotides.

In embodiments of the invention, a nascent strand (i.e., a segment formed during a polymerization reaction) shares sequence identity to a contiguous segment of a nucleic acid molecule having a length that is no more than about 95% of the entire length of the target nucleic acid molecule, or no more than about 75% of the entire length of the target nucleic acid molecule, or no more than about 50% of the entire length of the target nucleic acid molecule. "Length" in this context can be characterized by the number of nucleotides or nucleotide analogs in the nucleic acid molecule. For example, single-stranded nucleic acid molecules each having a sequence AATGCACT (SEQ ID NO: 7) can be said to have the same length.

Polymerization Reactions

In various embodiments of the invention, methods involve providing a polymerization environment comprising an array of optical confinements. A mixture is provided in the optical confinement, the mixture comprising: 1) a plurality of similar or substantially similar nucleic acid molecules having sequences identical or essentially identical to a target nucleic acid molecule, 2) primers complementary to the nucleic acid molecules, 3) polymerization enzymes, and 4) more than one type of nucleotide or nucleotide analog to be incorporated into a plurality of nascent nucleic acid strands. Each nascent strand is preferably complimentary to a respective portion of a nucleic acid molecule.

Next, the mixture is subjected to a polymerization reaction under conditions suitable for formation of the nascent nucleic acid strands by template-directed polymerization. The optical confinements are illuminated with a light beam, and the nucleotides or the nucleotide analogs incorporated into each nascent nucleic acid strand are identified. In one embodiment, the optical confinements are illuminated once asynchronous polymerization reactions have been established.

In one embodiment of the invention, substantially similar primers are provided in the optical confinements such that the polymerization reactions commence at substantially similar locations on each of the nucleic acid molecules. In another embodiment of the invention, the primers provided in the optical confinements can be different, such that polymerization reactions commence at different locations of the nucleic acid molecules. In embodiments of the invention, substantially similar primers can complement (or pair with) at least 4, or at least 5, or at least 6, or at least 7, or at least 8, or at least 9, or at least 10 nucleotides in a nucleic acid molecule.

In one embodiment, a nucleic acid molecule is immobilized to an inner surface of an optical confinement. A nucleic acid molecule can be immobilized to the inner surface of an optical confinement by a number of ways. For example, the nucleic acid molecule can be immobilized onto an optical confinement by attaching (1) a primer or (2) a single-stranded nucleic acid molecule or (3) a double-stranded or partially double-stranded nucleic acid molecule. Thereafter, either (1) the nucleic acid molecule is hybridized to the attached primer, (2) a primer is hybridized to the immobilized nucleic acid molecule to form a primer-nucleic acid molecule complex, or (3) a recognition site for the polymerase is created on the double-stranded or partially double-stranded nucleic acid molecule (e.g., through interaction with accessory proteins, such as a primase). A nucleic acid polymerizing enzyme on the primer-nucleic acid molecule complex is provided in a position suitable to move along the nucleic acid molecule and extend the primer at the site of polymerization to form a nascent (growing) strand complementary to the nucleic acid molecule.

In another embodiment of the invention, the polymerization enzyme can first be attached to a surface of an optical confinement within the effective observation volume of the optical confinement, and in a position suitable for the nucleic acid molecule complex to move relative to the polymerization enzyme. A nucleic acid molecule and a primer complementary to a portion of the nucleic acid molecule can then be provided in the optical confinement. Nucleotides or nucleotide analogs can then be provided (either sequentially or as a mixture) to initiate strand polymerization.

One skilled in the art will appreciate that there are many ways of immobilizing nucleic acid molecules and enzymes onto the surface of an optical confinement, whether covalently or noncovalently bonded, via a linker moiety, or tethering them to an immobilized moiety. These methods are well known in the field of solid phase synthesis and microarrays. See, e.g., Beier et al., Nucleic Acids Res. 27:1970-1-977 (1999). Non-limiting exemplary binding moieties for attaching either nucleic acid molecules or polymerases to a solid support include streptavidin or avidin/biotin linkages, carbamate linkages, ester linkages, amide, thiolester, (N)-functionalized thiourea, functionalized maleimide, amino, disulfide, amide, hydrazone linkages, and among others. Antibodies that specifically bind to the nucleic acid molecules or polymerases can also be employed as the binding moieties. In addition, a silyl moiety can be attached to a nucleic acid directly to a substrate (such as, e.g., glass) using methods known in the art.

Where desired, the polymerases may be modified to contain one or more epitopes such as Myc, HA (derived from influenza virus hemagglutinin), poly-histadines, and/or FLAG, for which specific antibodies are available commercially. In addition, the polymerases can be modified to contain heterologous domains such as glutathione S-transferase (GST), maltose-binding protein (MBP), specific binding peptide regions (see, e.g., U.S. Pat. Nos. 5,723,584, 5,874,239 and 5,932,433, which are entirely incorporated by reference herein), or the Fc portion of an immunoglobulin. The respective binding agents for these domains, namely glutathione, maltose, and antibodies directed to the Fc portion of an immunoglobulin are available, and can be used to coat the surface of an optical confinement of the present invention.

The binding moieties or agents of either the polymerases or nucleic acid molecules they immobilize can be applied to the support by conventional chemical techniques which are well known in the art. In general, these procedures can involve standard chemical surface modifications of a support, incubation of the support at different temperature levels in different media comprising the binding moieties or agents, and possible subsequent steps of washing and cleaning.

Components for Detection of Sequence Information

The sequencing method of various embodiments can require the imaging of individual molecules confined in an optical confinement. The polymerase and/or the nucleotides are labeled with fluorophores that emit a distinguishable optical signal when a particular type of nucleotide is incorporated into the nascent strand. The sequence of the distinguishable signals is detected as the nucleotides or nucleotide analogs are sequentially added to the nascent strand within the optical confinement. In an embodiment of the invention, such detection is performed without the need to transfer, separation or washing away any reactant or by-product (e.g. fluorophore cleaved from a nucleotide) after each nucleotide addition event. In one aspect of this preferred embodiment, sequence detection is performed without adding reactants to the mixture prior to reading the next base sequence nucleotide to be incorporated.

Imaging individual molecules confined in the subject optical confinements is performed with the aid of an optical system. Such system typically comprises at least two elements, namely an excitation source and a photon detector. Numerous examples of these elements are described above.

In an embodiment of the invention, the excitation source is a laser, preferably a polarized laser. The choice of laser light will depend on the fluorophores attached to the different type of nucleotides and/or the polymerases. For most of the fluorophorescent compounds, the required excitation light is within the range of about 300 nm to about 700 nm. For proteinaceous fluorophores such as green-fluororescent protein and mutants thereof, the excitation wavelength may range from about 488 nm to about 404 nm. Those skilled in the art will know or will be able to ascertain the appropriate excitation wavelength to excite a given fluorophore by routine experimentation (see e.g., The Handbook—'A Guide to Fluorescent Probes and Labeling Technologies, Tenth Edition' (2005) (available from Invitrogen, Inc./Molecular Probes) previously incorporated herein by reference).

Another consideration in selecting an excitation source is the choice between one-photon and multiphoton excitation of fluorescence. Multiphoton excitation coupled with detection, also known as multiphoton micropscopy ("MPM"), provides enhanced sensitivity and spatial resolution. MPM is a form of laser-scanning microscopy that uses localized nonlinear excitation to excite fluorescence within a thin raster-scanned plane. In MPM, as in conventional laser-scanning confocal microscopy, a laser is focused and raster-scanned across the sample. The image consists of a matrix of fluorescence intensity measurements made by digitizing the detector signal as the laser sweeps back and forth across the sample. Two-photon excitation probabilities are extremely small, and focusing increases the local intensity at the focal point. Although two-photon excited fluorescence is usually the primary signal source in MPM, three-photon or more excited fluorescence and second or third-harmonic generation can also be used for imaging. See, e.g., a review of multiphoton micropscopy in Webb et al. Nature Biotechnology (2003) 21: (11) 1251-1409. A preferred MPM setup comprises MPM laser scanning microscopes and second-harmonic imaging, equipped with femtosecond mode-locked titanium sapphire lasers operating at wavelengths from about 700 to 1,000 nm. Such setup can capture more than about 100 photons per pixel in most of the conventional imaging multiphoton microscope.

The sequence of the distinguishable signals can also be detected by other optical systems comprising elements such as optical reader, high-efficiency photon detection system, photo multiplier tube, gate sensitive field effect transistors (FETs), nano-tube FETs, photodiode (e.g., avalanche photo diodes (APD)), camera, charge couple device (CCD), electron-multiplying charge-coupled device (EMCCD), intensified charge coupled device (ICCD) and confocal microscope.

A preferred combination comprises wide field CCD or ICCD and intensified video imaging microscopes with digital image processing capability, as well as Fluorescence Photobleaching Recovery (FPR) and Fluorescence Correlation Spectroscopy (FCS) coupled with confocal multiphoton capability and continuous data acquisition and control. Such a set up may further comprise modular instrument for quasi-elastic light scattering, laser DIC interferometry, correlation spectroscopy instrumentation, components of optical force microscopy, and Time Correlated Single Photon Counting (TCSPC).

These optical systems may also comprise optical transmission elements such as diffraction gratings, arrayed waveguide gratings (AWG), optic fibers, optical switches, mirrors, lenses (including microlens and nanolens), collimators. Other examples include optical attenuators, polarization filters (e.g., dichroic filter), wavelength filters (low-pass, band-pass, or high-pass), wave-plates, and delay lines. In some embodiments, the optical transmission element can be planar waveguides in optical communication with the arrayed optical confinements.

These and other optical components known in the art can be combined and assembled in a variety of ways to effect detection of the distinguishable signals emitted from the sequencing reaction. Preferred devices allow parallel data collection using arrays having a large number of optical confinements, where simultaneous and independent sequencing of nucleic acids takes place. In one aspect, the preferred system can collect and process signals from more than 104 optical confinements, more than 2×104 optical confinements, or more than 105 optical confinements, or more than 2×105 optical confinements, or preferably more than 106, or preferably more than 2×106 optical confinements, and even more preferably more than 107 or 2×107 optical confinements. In another aspect, the preferred setup can monitor in real time the simultaneous and independent sequencing of nucleic acids at a speed of about 1 base per second, preferably at a speed of about 10 bases per second, more preferably at a speed of about 100 bases per second and even more preferably at 1,000 bases per second. As such, the massive parallelism coupled with the rapid sequencing reaction can provide an overall sequencing output greater than 100,000 bases per second. The overall output can be scaled up to at least 1 megabase per second, preferably 10 or more megabases per second. Further by obtaining such data from multiple different sequence fragments e.g., from two or more different reaction volumes, one can obtain independent sequences, e.g. from contiguous fragments of genomic DNA, allowing the high rate of throughput that is directly applicable to genomic sequencing.

Reagents

In embodiments of the invention, nucleotides or nucleotides analogs are provided in optical confinements comprising nucleic acid molecules and polymerization enzymes to commence polymerization of nascent strands.

Templates to be sequenced can include any type of nucleic acid molecule known to those skilled in the art. Nucleic acid molecules can include DNA, RNA, mRNA, peptide nucleic acid (PNA), morpholino nucleic acid, locked nucleic acid (LNA), glycol nucleic acid (GNA), and threose nucleic acid (TNA).

Primers discussed herein can include primers for initiating polymerization, blocking primers, forward primers, reverse primers, sequencing primers, or any of a number of nucleic acid molecules known to those skilled in the art. In some instances, the primers can be photoactivatable or photosensitive primers. The photoactivatable primers can include caged 3' end primers which can be photoactivated specifically and temporally.

The various types of nucleotides utilized in accordance with the sequencing methods of various aspects and embodiments are conjugated with detectable labels so that a photon detector can detect and distinguish their presence within the subject optical confinements. Preferred labels are luminescent labels, and especially fluorescent or chromogenic labels.

A variety of functional groups used as detectable labels in nucleotides has been developed in the art. Table 1 (see below) lists numerous examples of such functional groups. Additional examples are described in U.S. Pat. No. 6,399,335, published U.S. Patent Application No. 2003/0124576, and The Handbook—'A Guide to Fluorescent Probes and Labeling Technologies, Tenth Edition' (2005) (available from Invitrogen, Inc.,/Molecular Probes), all of which are entirely incorporated herein by reference.

TABLE 1

Exemplary detectable label functional groups

| | |
|---|---|
| 4-aminophenol | 6-aminonaphthol |
| 4-nitrophenol | 6-nitronaphthol |
| 4-methylphenol | 6-chloronaphthol |
| 4-methoxyphenol | 6-bromonaphthol |
| 4-chlorophenol | 6-iodonaphthol |
| 4-bromophenol | 4,4'-dihydroxybiphenyl |
| 4-iodophenol | 8-hydroxyquinoline |
| 4-nitronaphthol | 3-hydroxypyridine |
| 4-aminonaphthol | umbelliferone |
| 4-methylnaphthol | Resorufin |
| 4-methoxynaphthol | 8-hydroxypyrene |
| 4-chloronaphthol | 9-hydroxyanthracene |
| 4-bromonaphthol | 6-nitro9-hydroxyanthracene |
| 4-iodonaphthol | 3-hydroxyflavone |
| 6-methylnaphthol | fluorescein |
| 6-methoxynaphthol | 3-hydroxybenzoflavone |

Using these or other suitable functional groups known in the art, a vast diversity of fluorophores suitable for the present sequencing method can been generated. They include, without limitation, 4-acetamido-4'-isothiocyanatostilbene-2,2'disulfonic acid, acridine and derivatives such as acridine and acridine isothiocyanate, 5-(2'-aminoethyl)aminonaphthalene-1-sulfonic acid (EDANS), 4-amino-N-[3-vinylsulfonyl)phenyl]naphthalimide-3,5 disulfonate (Lucifer Yellow VS), N-(4-anilino-1-naphthyl)maleimide, anthranilamide, Brilliant Yellow, coumarin and derivatives such as coumarin, 7-amino-4-methylcoumarin (AMC, Coumarin 120), 7-amino-4-trifluoromethylcouluarin (Coumaran 151); cyanosine; 4',6-diaminidino-2-phenylindole (DAPI); 5',5'-dibromopyrogallol-sulfonephthalein (Bromopyrogallol Red); 7-diethylamino-3-(4'-isothiocyanatophenyl)-4-methylcoumarin; diethylenetriamine pentaacetate; 4,4'-diisothiocyanatodihydro-stilbene-2,2'-disulfonc acid; 4,4'-diisothiocyanatostilbene-2,2'-disulfonic acid; 5-[dimethylamino] naphthalene-1-sulfonyl chloride (DNS, dansyl chloride); 4-(4'-dimethylaminophenylazo)benzoic acid (DABCYL); 4-dimethylaminophenylazophenyl-4'-isothiocyanate (DABITC); eosin and derivatives such as eosin and eosin isothiocyanate; erythrosin and derivatives such as erythrosin B and erythrosin isothiocyanate; ethidium; fluorescein and derivatives such as 5-carboxyfluorescein (FAM), 5-(4,6-dichlorotriazin-2-yl)aminofluorescein (DTAF), 2'7'-dimethoxy-4'5'-dichloro-6-carboxyfluorescein (JOE), fluorescein, fluorescein isothiocyanate (FITC), and QFITC (XRITC); fluorescamine; IR144; IR1446; Malachite Green isothiocyanate; 4-methylumbelliferone; ortho cresolphthalein; nitrotyrosine; pararosaniline; Phenol Red; B-phycoerythrin; o-phthaldialdehyde; pyrene and derivatives such as pyrene, pyrene butyrate and succinimidyl 1-pyrene butyrate; Reactive Red 4 (Cibacron® Brilliant Red 3B-A); rhodamine and derivatives such as 6-carboxy-X-rhodamine (ROX), 6-carboxyrhodamine (R6G), lissamine rhodamine B sulfonyl chloride, rhodamine (Rhod), rhodamine B, rhodamine 123, rhodamine X isothiocyanate, sulforhodamine B, sulforhodamine 101 and sulfonyl chloride derivative of sulforhodamine 101 (Texas Red); N,N,N',N'-tetramethyl-6-carboxyrhodamine (TAMRA); tetramethyl rhodamine; tetramethyl rhodamine isothiocyanate (TRITC); riboflavin; rosolic acid and terbium chelate derivatives. Additional fluorophores applicable for the subject sequencing methods are disclosed in U.S. Pat. No. 5,866,366 and WO 01/16375, both of which are incorporated herein by reference.

The labels can be attached to the phosphate backbone, on the base, on the ribose unit, or a combination thereof. Preferred labels are those that do not substantially impede the continuous addition of nucleotides in a sequencing reaction. Such labels include those linked to the alpha phosphate, the beta phosphate, the terminal phosphate, or the delta or more distal phosphates in tetra, penta or hexa phosphate nucleotides, or the base unit of a nucleotide.

Nucleotides or nucleotide analogs comprising labeled terminal phosphates (e.g., the gamma phosphate, as in dNTP), are particularly preferred because no additional means is required to remove the label in the sequencing procedure. During nucleic acid polymerization, the bond cleavage in the nucleotide occurs between the alpha and the beta phosphate, causing the beta and terminal phosphate (e.g., the gamma phosphate as in dNTP) to be released from the site of polymerization. As such, the label attached to the terminal phosphate is separated from the nascent strand once the nucleotide is being incorporated. In general, terminal-phosphate-linked nucleotides may comprise three or more phosphates, typically about three to about six phosphates, preferably about three to about five phosphates. Table 2 (see below) lists numerous examples of nucleotides with labeled terminal phosphates. Many other terminal-phosphate-linked nucleotides have been developed and are detailed in U.S. patent application number 2003/0124576, which is incorporated herein by reference in its entirety.

TABLE 2

Adenosine-5'-(γ-4-nitrophenyl)triphosphate
Guanosine-5'-(γ-4-nitrophenyl)triphosphate
Cytosine-5'-(γ-4-nitrophenyl)triphosphate
Thymidine-5'-(γ-4-nitrophenyl)triphosphate
Uracil-5'-(γ-4-nitrophenyl)triphosphate
3'-azido-3'-deoxythymidine-5'-(γ-4-nitrophenyl)triphosphate
3'-azido-2',3'-dideoxythymidine-5'-(γ-4-nitrophenyl)triphosphate
2',3'-didehydro-2',3'-dideoxythymidine-5'-(γ-4-nitrophenyl)triphosphate
Adenosine-5'-(γ-4-aminophenyl)triphosphate
Adenosine-5'-(γ-4-methylphenyl)triphosphate
Adenosine-5'-(γ-4-methoxyphenyl)triphosphate
Adenosine-5'-(γ-4-chlorophenyl)triphosphate
Adenosine-5'-(γ-4-bromophenyl)triphosphate
Adenosine-5'-(γ-4-iodophenyl)triphosphate
Adenosine-5'-(γ-4-nitronaphthyl)triphosphate
Adenosine-5'-(γ-4-aminonaphthyl)triphosphate
Adenosine-5'-(γ-4-methylnaphthyl)triphosphate
Adenosine-5'-(γ-4-methoxynaphthyl)triphosphate

TABLE 2-continued

Adenosine-5'-(γ-4-chloronaphthyl)triphosphate
Adenosine-5'-(γ-4-bromonaphthyl)triphosphate
Adenosine-5'-(γ-4-iodonaphthyl)triphosphate
Adenosine-5'-(γ-6-methylnaphthyl)triphosphate
Adenosine-5'-(γ-6-methoxynaphthyl)triphosphate
Adenosine-5'-(γ-6-aminonaphthyl)triphosphate
Adenosine-5'-(γ-6-nitronaphthyl triphosphate
Adenosine-5'-(γ-6-chloronaphthyl)triphosphate
Adenosine-5'-(γ-6-bromonaphthyl)triphosphate
Adenosine-5'-(γ-6-iodonaphthyl)triphosphate
Adenosine-5'-(γ-4'-hydroxybiphenyl)triphosphate
Adenosine-5'-(γ-8-quinolyl)triphosphate
Adenosine-5'-(γ-3-pyridyl)triphosphate
Adenosine-5'-(γ-umbelliferone)triphosphate
Adenosine-5'-(γ-resorufin)triphosphate
Adenosine-5'-(γ-pyrene)triphosphate
Adenosine-5'-(γ-anthracene)triphosphate
Adenosine-5'-(γ-6-nitroanthracene)triphosphate
Adenosine-5'-(γ-flavonyl)triphosphate
Adenosine-5'-(γ-fluorescein)triphosphate
Adenosine-5'-(γ-benzoflavone)triphosphate
Adenosine-5'-(γ-(4-nitrophenyl)-γ-(4-aminophenyl)triphosphate
Adenosine-5'-(γ-(4-nitrophenyl)-γ-(4-nitronaphthyl)triphosphate Nucleotide or nucleotide analogs comprising modified phosphate backbones can also be used. For example, the modified component can be a phosphordiamidate, methylphosphonate, alkyl phosphotriester, formacetal, phosphorodithioate, phosphothioate, phosphoramidothioate, phosphoramidate, or an analog thereof.

In some embodiments, the nucleotides or nucleotide analogs used in the present invention are reversible extension terminators comprising reversible blocking groups. In some embodiments, the blocking group on a reversible extension terminator is linked to a detectable label. In other embodiments, the blocking group and the detectable label are located on different positions of a nucleotide. In yet other embodiments, the blocking group is also a label. The label can be attached to a linker such as PEG, a proline chain, a glycine-serine linker, or any other linking molecule known to those skilled in the arts.

An illustrative reversible extension terminator comprises a labeled ribose unit at the 3' end. Each label on the ribose unit, typically acts as a reversible blocking group that must be removed before the next nucleotide addition event can take place during a polymerization reaction. Preferred 3'-ribose labels comprise photo-removable functional groups that can be deprotected upon exposure to a light beam at a suitable wavelength.

In another example, the reversible blocking group is located at the 2' or the 4' position of the ribose unit of a nucleotide. In yet another embodiment, the reversible blocking group is linked to or conjugated to the base (adenine, thymine, cytosine, guanine, or uracil) a nucleotide. Non-limiting examples of reversible blocking groups, and especially photocleavable blocking groups include, but are not limited to, those molecules described in U.S. patent application Ser. Nos. 11/925,675, 11/925,650, 11/925,607, 11/626,610, 11/229,376, 11/228,925, 11/228,376, 10/944,106 and 60/649,009, which are entirely incorporated herein by reference.

The wavelength of electromagnetic radiation (also "radiation" or "light" herein) used to cleave the photocleavable blocking groups will depend on the choice of the blocking group. The wavelength may range from about 320 nm to about 800 nm. In some embodiment, the wavelength for cleaving the blocking group is about the same as the wavelength used to detect the label. In other embodiments, the wavelength for cleaving the blocking group is different from the wavelength used to detect the label.

In some embodiments, it is advantageous to use a mixture of labeled nucleotides that is substantially free of unlabeled nucleotides. Such composition and the uses thereof for sequencing are detailed in U.S. Patent Application Ser. No. 60/651,846, which is entirely incorporated herein by reference. Briefly, the composition is prepared by treating a mixture comprising labeled and unlabeled nucleotides or nucleotide analogs with an agent that specifically modifies unlabeled or incorrectly labeled nucleotides or nucleotide analogs to reduce their ability to be used in a hybridization or sequencing assay. Preferably, the agent used specifically modifies unlabeled or incorrectly labeled nucleotides analogs to render them incapable of being used in a hybridization or sequencing assay. For example, the nucleotides can be modified so that they no longer contain structures generally needed for base pairing in a hybridization or template-directed sequencing assay. In some embodiments, for example, base units of the nucleotides are modified. In some embodiments, phosphate groups, preferably terminal phosphate groups, of the nucleotides or nucleotide analogs are modified to yield molecules that are incorporated to a lesser extent into a nascent nucleic acid strand during a template-directed polymerization reaction. In more embodiments of the invention, the terminal phosphate groups of a nucleotide or nucleotide analogs are modified to yield molecules that cannot or that substantially cannot be incorporated into a nascent nucleic acid strand during a template-directed polymerization reaction.

The agents can comprise one or more enzymes. A variety of enzymes known in the art are suitable for modifying the nucleotides or nucleotide analogs, e.g. by cleaving or altering the configuration of the sugar, base, or phosphates, so as to disrupt the specific Watson Crick base pairing. Exemplary agents include, but are not limited to, guanine or adenine P-ribosyl transferase, purine nucleoside phosphorylase, AMP nuleosidase, nucleoside deoxyribosyl transferase for purines, and orotate P-ribosyl transferase, thymidine phosphorylase, thymidine or uridine nucleosidase, uridine phosphorylase, pyrimidine nucleoside phosphorylase nucleoside deoxyribosyl transferase.

Enzymes applicable for modifying the terminal phosphate groups of nucleotides or nucleotide analogs include a wide array of phosphatases. An example of such enzyme is Shrimp Alkaline Phosphatase (SAP) that can remove the gamma and beta phosphates from a deoxynucleoside triphosphate (dNTP). The enzyme can convert specifically unlabeled dNTP into a nucleoside monophosphate dNMP which is generally incapable of being utilized by a polymerase enzyme in a template-directed sequencing reaction. It has been shown, that this phosphatase selectively modify nucleotides that are not labeled, e.g. at the terminal phosphate. Therefore, in a mixture of terminal phosphate-labeled and unlabeled nucleotides, the SAP will preferentially act on unlabeled nucleotides, leaving a larger proportion of labeled nucleotides available for incorporation in a sequencing reaction.

Other suitable phosphatases that can be used include but are not limited to calf intestinal alkaline phosphatases, and/or phosphatases of other mammals, crustaceans, and other animals. Examples of phosphatases that may be useful practicing the present invention can be found in U.S. Patent Publication Nos. 2004/0203097, 2004/0157306, 2004/0132155 and 2004/0110180, which are entirely incorporated herein by reference.

Any other naturally occurring or synthetic phosphatases or phosphatases made by recombinant DNA technology can also be used so long as they specifically or preferentially convert unlabeled nucleotides or analogs (as compared to labeled nucleotides), to molecules that are substantially incapable of being utilized by a polymerization enzyme. Directed molecular evolution can also be used to enhance and extend the activity of related enzymes to yield the desired property described above. A wide variety of mutagenesis techniques, both in silicon and in situ, are available in the art. An example of a mutagenesis or screening assay for generating such enzymes can involve a first test for abrogation of polymerization in the system with unlabeled nucleotides, and a second screen checking for the retention of polymerization activity in the presence of labeled nucleotides. Both of these screens can be performed in the context of a highly multiplexed parallel assay. Enzymes showing some beneficial specificity can be retained, mutated by some method, and then re-screened. Methods such as these have been shown to produce many orders of magnitude improvement in specificity and performance.

Enzymes capable of selectively or preferentially modifying a subset of unlabeled nucleotides can also be employed. For example, creatine kinase enzyme is specific for the removal of a phosphate from adenoside triphosphate, and will not act on other bases. Other enzymes that selectively or preferentially act on one or more types of unlabeled nucleotides can also be used.

The nucleotide modifying enzymes described above can be used to pre-treat the nucleotides or nucleotide analogs, or can be used in the hybridization and/or sequencing reaction mixture, e.g., along with other hybridization or sequencing reagents.

The reaction conditions under which the modification of the nucleotides takes place will vary depending on the choice of the modifying enzymes. In one aspect, the conditions may be set within the following parameters: pH is between 4.0 and 12.0, more preferably between pH 6.0 and 10.0, more preferably between 7.0 and 9.0, more preferably less than 8, more preferably between 7 and 8, and most preferably pH 7.5 and 8.5, preferably controlled by a buffer. The buffer can be Tris-based preferably at pH 7.5 to pH 8.5. Other buffers may be used such as, but not limited to: organic buffers such as MOPS, HEPES, TRICINE, etc., or inorganic buffers such as phosphate or acetate. Buffers or other agents may be added to control the pH of the solution thereby increasing the stability of the enzymes. Where desired, reducing agent such as but not limited to dithiotreitol (DTT) or 2-mercaptoethanol may be added to limit enzyme oxidation that might adversely affect stability of the enzymes. The choice of specific reaction conditions including various buffers and pH conditions is within the skill of practitioners in the field, and hence is not further detailed herein.

Upon completion of the pre-treatment, the enzymes can be heat-inactivated by raising the reaction temperature to at least about 65° C., preferably between about 65° C. to about 80° C. Alternatively, the enzymes can be depleted from the reaction mixture by, e.g., centrifugation through a filter (e.g., Millipore) that has a molecular weight cutoff smaller than the size of the enzyme.

After the treatment, the mixture generally comprises less than about 30%, preferably less than about 20%, more preferably less than about 10%, more preferably less than about 5%, more preferably less than about 1%, more preferably less than about 0.5%, or more preferably less than about 0.1%, and even more preferably less than 0.01% of unlabeled nucleotides or unlabeled nucleotide analogs. This enriched mixture of labeled nucleotides or nucleotide analogs is particularly useful for high-resolution detection of the labeled nucleotides in a single-molecule sequence reaction.

Importantly, the result of the foregoing treatment is a process for synthesis of nucleic acids, preferably for elucidating a template sequence using substantially only nucleotides, e.g., substantially complete replacement of native nucleotides with nucleotide analogs, and particularly labeled analogs. Such template dependant synthesis in the presence of substantially only nucleotide analogs, and particularly labeled analogs, also referred to as substantially complete replacement, in sequencing operations is considerably different from previously described sequencing methods where a single nucleotide is substituted with a labeled chain terminating nucleotide among the remaining three natural nucleotides, or where a polymerase template complex are interrogated with only one analog at a time to determine whether such analog is incorporated.

Another type of suitable nucleotide for the subject sequencing methods allows detection via fluorescence resonance energy transfer (FRET). In FRET, an excited fluorophore (the donor) transfers its excited state energy to a light absorbing molecule (the acceptor) in a distance-dependent manner. The limitation on the distance over which the energy can travel allows one to discern the interactions between labeled molecules and entities in close proximity. Nucleotides of this type can comprise a donor fluorophore attached to the base, ribose or preferably the phosphate backbone (e.g., attached to the terminal phosphate), and an acceptor fluorophore attached to the base, ribose or the phosphate backbone where the donor is not attached. In an embodiment of the invention, the donor fluorophore is attached to the terminal phosphate, and an acceptor fluorophore is linked to the base or the ribose unit of the nucleotide. Upon incorporation of this type of nucleotide into the nascent strand, a fluorescent signal can be detected which can be caused by the release of polyphosphate that is no longer quenched. By determining the order of the fluorescent poly-phosphate that is released upon incorporating a complementary nucleotide during the polymerization event, one can deduce the base sequence of the target nucleic acid. Additional examples of this type of nucleotide are disclosed in U.S. Patent Publication No. 2003/0194740, which is incorporated herein by reference.

In another embodiment, the donor fluorophore can be present in a nucleotide, and the acceptor is located in the polymerase, or vice versa. Where desired, the fluorophore in the polymerase can be provided by a green fluorescent protein (GFP) or a mutant thereof that has a different emission and/or absorption spectrum relative to the wildtype green fluorescent protein. For example, the GFP mutant H9-40 (Tsien et al., Ann. Rev. Biochem. 67: 509 (1998)) which is excited at 399 nm and emits at 511 nm, may serve as a donor fluorophore for use with BODIPY, fluorescein, rhodamine green and Oregon green. In addition, tetramethylrhodamine, Lissamine™, Texas Read and napthofluorescein can be used as acceptor fluorophores with this GFP mutant.

Other representative donors and acceptors capable of fluorescence energy transfer include, but are not limited to, 4-acetamido-4'-isothiocyanatostilbene-2,2'disulfonic acid; acridine and derivatives: acridine, acridine isothiocyanate; 5-(2'-aminoethyl)aminonap-hthalene-1-sulfonic acid (EDANS); 4-amino-N-[3-vinylsulfonyl)phenyl]naphth-alimide-3,5 disulfonate; N-(4-anilino-1-naphthyl)maleimide; anthranilamide; BODIPY; Brilliant Yellow; coumarin and derivatives: coumarin, 7-amino-4-methylcoumarin (AMC, Coumarin 120), 7-amino-4-trifluoromethylcouluarin (Coumaran 151); cyanine dyes; cyanosine; 4',6-diaminidino-2-phenylindole (DAPI); 5',5''-dibromopyrogallol-sulfonaphthalein (Bromopyrogallol Red); 7-diethylamino-3-(4'-isothiocyanatophenyl)-4-methylcoumarin; diethylenetriamine pentaacetate; 4,4'-diisothiocyanatodihydro-stilbene-2,-2'-disulfonic acid; 4,4'-diisothiocyanatostilbene-2,2'-disulfonic acid; 5-[dimethylamino]naphthalene-1-sulfonyl chloride (DNS, dansylchloride); 4-dimethylaminophenylazophenyl-4'-isothiocyanate (DABITC); eosin and derivatives: eosin, eosin isothiocyanate, erythrosin and derivatives: erythrosin B, erythrosin, isothiocyanate; ethidium; fluorescein and derivatives: 5-carboxyfluorescein (FAM), 5-(4,6-dichlorotriazin-2-yl)aminofluorescein (DTAF), 2',7'-dimethoxy4'5'-dichloro-6-carboxyfluorescein (JOE), fluorescein, fluorescein isothiocyanate, QFITC, (XRITC); fluorescamine; IR144; IR1446; Malachite Green isothiocyanate; 4-methylumbelliferoneortho cresolphthalein; nitrotyrosine; pararosaniline; Phenol Red; B-phycoerythrin; o-phthaldialdehyde; pyrene and derivatives: pyrene, pyrene butyrate, succinimidyl 1-pyrene; butyrate quantum dots; Reactive Red 4 (Cibacron™ Brilliant Red 3B-A) rhodamine and derivatives: 6-carboxy-X-rhodamine (ROX), 6-carboxyrhodamine (R6G), lissamine rhodamine B sulfonyl chloride rhodamine (Rhod), rhodamine B, rhodamine 123, rhodamine X isothiocyanate, sulforhodamine B, sulforhodamine 101, sulfonyl chloride derivative of sulforhodamine 101 (Texas Red); N,N,N',N'-tetramethyl-6-carboxyrhodamine (TAMRA); tetramethyl rhodamine; tetramethyl rhodamine isothiocyanate (TRITC); riboflavin; rosolic acid; terbium chelate derivatives; Cy 3; Cy 5; Cy 5.5; Cy 7; IRD 700; IRD 800; La Jolla Blue; phthalo cyanine; and naphthalo cyanine.

In alternative configurations, both donor and acceptor fluorophores may be present upon each nucleotide analog, where the donor provides a substantially uniform excitation spectrum, but donates energy to an acceptor that provides an emission spectrum that is different for each type of analog, e.g., A, T, G, or C. Such configurations provide an ability to utilize a single excitation source for multiple different emission profiles, reducing energy input requirements for the systems utilized.

In addition, xanthene dyes, including fluoresceins and rhodamine dyes can be used as donor and acceptor pairs. Many of these dyes contain modified substituents on their phenyl moieties which can be used as the site for bonding to the terminal phosphate or the base of a nucleotide. Where desired, acceptors acting as quenchers capable of quenching a wide range of wavelengths of fluorescence can be used. Representative examples of such quenchers include 4-(4'-dimethylaminophenylaz-o)-benzoic acid (DABCYL), dinitrophenyl (DNP) and trinitrophenyl (TNP).

The polymerization enzymes suitable for the present invention can be any nucleic acid polymerases that are capable of catalyzing template-directed polymerization with reasonable synthesis fidelity. The polymerases can be DNA polymerases or RNA polymerases, a thermostable polymerase or a thermally degradable polymerase wildtype or modified. Non-limiting examples for suitable thermostable polymerases include polymerases from *Thermus aquaticus, Thermus caldophilus, Thermus filiformis, Bacillus caldotenax, Bacillus stearothermophus, Thermus thermophilus, Pyrococcus woesei, Pyrococcus furiosus, Thermococcus litoralis*, and *Thermotoga maritima*. Useful thermodegradable polymersases include *E. coli* DNA polymerase, the Klenow fragment of *E. coli* DNA polymerase, T4 DNA polymerase, T7 DNA polymerase.

Additional examples of polymerization enzymes that can be used to determine the sequence of nucleic acid molecules include *E. coli* T7, T3, SP6 RNA polymerases and AMV, M-MLV and HIV reverse transcriptases. The polymerase can be bound to the primed target nucleic acid sequence at a primed single-stranded nucleic acid, an origin of replication, a nick or gap in a double-stranded nucleic acid, a secondary structure in a single-stranded nucleic acid, a binding site created by an accessory protein, or a primed single-stranded nucleic acid.

In one embodiment of the invention, the polymerization enzymes exhibit enhanced efficiency as compared to the wildtype enzymes for incorporating unconventional or modified nucleotides, e.g., nucleotides linked with fluorophores. Recombinant DNA techniques can be used to modify the wildtype enzymes. Such techniques typically involve the construction of an expression vector or a library of expression vector, a culture of transformed host cells under such condition such that expression will occur. Selection of the polymerases that are capable of incorporating unconventional or modified nucleotides can be carried out using any conventional sequencing methods as well as the sequencing methods disclosed herein.

In another embodiment of the invention, sequencing is carried out with polymerases exhibiting a high degree of processivity, i.e., the ability to synthesize long stretches of nucleic acid by maintaining a stable nucleic acid/enzyme complex. A processive polymerase can typically synthesize a nascent strand over about 10 kilo bases. With the aid of accessory enzymes (e.g., helicases/primases), some processive polymerases can synthesize even over 50 kilobases. For instance, it has been shown that T7 DNA polymerase complexed with helicase/primase can synthesize several 100 kilobases of nucleotides while maintaining a stable complex with the target nucleic acid (Kelman et al., "Processivity of DNA Polymerases: Two Mechanisms, One Goal" Structure 6: 121-125 (1998)).

In another embodiment of the invention, sequencing is performed with polymerases capable of rolling circle replication, i.e., capable of replicating circular DNA templates including but not limited to plasmids and bacteriophage DNA. A rolling circle polymerase can exhibit strand-displacement activity, and can have reduced or essentially no 5' to 3' exonuclease activity. Strand displacement results in the synthesis of tandem copies of a circular DNA template, thus allowing re-sequencing the same DNA template more than once. Re-sequencing the same DNA template greatly enhances the chances to detect any errors made by the polymerase, because the same errors unlikely would be repeated by the polymerase and the same error certainly would not be exponentially amplified as in a polymerase chain reaction.

Non-limiting examples of rolling circle polymerases suitable for the present invention include but are not limited to T5 DNA polymerase (Chatterjee et al., Gene 97:13-19 (1991)), and T4 DNA polymerase holoenzyme (Kaboord and Benkovic, Curr. Biol. 5:149-157 (1995)), phage M2 DNA polymerase (Matsumoto et al., Gene 84:247 (1989)), phage PRD1 DNA polymerase (Jung et al., Proc. Natl. Aced. Sci. USA 84:8287 (1987), and Zhu and Ito, Biochim. Biophys. Acta. 1219:267-276 (1994)), Klenow fragment of DNA polymerase I (Jacobsen et al., Eur. J. Biochem. 45:623-627 (1974)).

A class of rolling circle polymerases can utilize protein priming as a way of initiating replication. Exemplary polymerases of this class are modified and unmodified DNA polymerase, chosen or derived from the phages Φ29, PRD1, Cp-1, Cp-5, Cp-7, Φ15, Φ1, Φ21, Φ25, BS 32 L17, PZE, PZA, Nf, M2Y (or M2), PR4, PR5, PR722, B103, SF5, GA-1, and related members of the Podoviridae family. Specifically, the wildtype bacteriophage Φ29 genome consists of a linear double-stranded DNA (dsDNA) of 19,285 base pairs, having a terminal protein (TP) covalently linked to each 5' end. To initiate replication, a histone-like viral protein forms a nucleoprotein complex with the origins of replication that likely contributes to the unwinding of the double helix at both DNA ends (Serrano et al., The EMBO Journal 16(9): 2519-2527 (1997)). The DNA polymerase catalyses the addition of the first dAMP to the hydroxyl group provided by the TP. This protein-primed event occurs opposite to the second 3' nucleotide of the template, and the initiation product (IP-dAMP) slides back one position in the DNA to recover the terminal nucleotide. After initiation, the same DNA polymerase replicates one of the DNA strands while displacing the other. The high processivity and strand displacement ability of Φ29 DNA polymerase makes it possible to complete replication of the Φ29 TP-containing genome (TP-DNA) in the absence of any helicase or accessory processivity factors (reviewed by Serrano et al., The EMBO Journal 16(9): 2519-2527 (1997)).

Modified Φ29 DNA polymerases having reduced 5' to 3' exonuclease activity have also been described U.S. Pat. Nos. 5,198,543 and 5,001,050, both being incorporated herein). These polymerases are particularly desirable for sequencing as the 5' to 3' exonucleases, if present excessively, may degrade the nascent strand being synthesized.

Strand displacement can be enhanced through the use of a variety of accessory proteins. They include but are not limited to helicases (Siegel et al., J. Biol. Chem. 267:13629-13635 (1992)), herpes simplex viral protein ICP8 (Skaliter and Lehman, Proc. Natl. Acad. Sci. USA 91(22):10665-10669 (1994)), single-stranded DNA binding proteins (Rigler and Romano, J. Biol. Chem. 270:8910-8919 (1995)), adenovirus DNA-binding protein (Zijderveld and van der Vliet, J. Virology 68(2):1158-1164 (1994)), and BMRF1 polymerase accessory subunit (Tsurumi et al., J. Virology 67(12):7648-7653 (1993)).

In an embodiment of the invention, the sequence reaction involves a single complex of strand-displacement polymerization enzyme and a circular target DNA, which is immobilized to an optical confinement. Upon mixing the labeled nucleotides or nucleotide analogs and the primers, the strand-displacement polymerization enzyme directs the synthesis of a nascent strand and a time sequence of incorporating the various types of labeled nucleotides or nucleotide analogs into the nascent strand is registered. Where desired, the strand-displacement polymerase is allowed to synthesize multiple tandem repeats of the target DNA, and thus effecting re-sequencing the same circular DNA target multiple times. It is preferably to register the time sequence of the nucleotides or nucleotide analogs incorporated into at least two tandem repeats of the target DNA molecule, more preferably at least about three to about ten or about three to about one hundred tandem repeats, and preferably no more than about one million repeats. This multiple rounds of or redundant sequencing can take place under an isothermal condition and/or at ambient temperature.

Using the subject method, sequencing can be carried out at the speed of at least 1 base per second, preferably at least 10 bases per second, more preferably at least 100 bases per second. It has been reported that polymerases can polymerize 1,000 bases per second in vivo and 750 bases per second in vitro (see, e.g. Kelman et al., "Processivity of DNA Polymerases: Two Mechanisms, One Goal," Structure 6: 121-125 (1998); Carter et al., "The Role of Exonuclease and Beta Protein of Phage Lambda in Genetic Recombination. II. Substrate Specificity and the Mode of Action of Lambda Exonuclease," J. Biol. Chem. 246: 2502-2512 (1971); Tabor et al., "*Escherichia coli* Thioredoxin Confers Processivity on the DNA Polymerase Activity of the Gene 5 Protein of Bacteriophage T7," J. Biol. Chem. 262: 16212-16223 (1987); and Kovall et al., "Toroidal Structure of Lambda-Exonuclease" Science 277: 1824-1827 (1997), which are hereby incorporated by reference).

Reaction Conditions

The sequencing procedures of the present invention are performed under any conditions such that template-directed polymerization can take place using a polymerization enzyme. In one aspect, the substrates of the polymerization enzyme, namely the various types of nucleotides present in the sequence reaction, are adjusted to a physiologically relevant concentration. For example, the nucleotides used in the sequencing reaction are present at a concentration about Michaelis constant of the polymerization enzyme. Such concentration typically ranges from about 1 micromolar to about 50 micromolar or about 100 micromolar.

The sequencing procedures can also be accomplished using less than four labels. With three labels, the sequence can be deduced from sequencing a nucleic acid strand (1) if the fourth base can be detected as a constant dark time delay between the signals of the other labels, or (2) unequivocally by sequencing both nucleic acid strands, because in this case one obtains a positive fluorescence signal from each base pair. Another possible scheme that utilizes two labels is to have one base labeled with one fluorophore and the other three bases with another fluorophore. In this case, the other three bases do not give a sequence, but merely a number of bases that occur between the particular base being identified by the other fluorophore. By cycling this identifying fluorophore through the different bases in different sequencing reactions, the entire sequence can be deduced from sequential sequencing runs. Extending this scheme of utilizing two labels only, it is even possible to obtain the full sequence by employing only two labelled bases per sequencing run.

The sequencing procedures can be performed under an isothermal condition, at ambient temperature, or under thermal cycling condition. The choice of buffers, pH and the like is within the skill of practitioners in the art, and hence is not detailed herein.

Kits

The present invention also encompasses kits containing the optical confinement arrays of this invention. Kits embodied by this invention include those that allow characterizing molecules and/or monitoring chemical reactions at a single-molecule level. Each kit usually comprises the devices and reagents which render such characterization and/or monitoring procedure possible. Depending on the intended use of the kit, the contents and packaging of the kit will differ. Where the kit is for DNA sequencing, the kit typically comprises: (a) an array of optical confinements, preferably zero-mode waveguides of the present invention, that permits resolution of individual molecules or the reaction of individual molecules, such as those that are present at a concentration higher than about 1 micromolar; (b) sequencing reagents typically including polymerases, aqueous buffers, salts, primers, and nucleotides or nucleotide analogs. Where desired, "control" nucleic acids of known sequences can be included to monitor the accuracy or progress of the sequencing process.

The reagents can be supplied in a solid form, immobilized form, and/or dissolved/suspended in a liquid buffer suitable for inventory storage, and later for exchange or addition into the reaction medium when the test is performed. Suitable individual packaging is normally provided. The kit can optionally provide additional components that are useful in the procedure. These optional components include, but are not limited to, buffers, capture reagents, developing reagents, labels, reacting surfaces, control samples, instructions, and interpretive information. Diagnostic or prognostic procedures using the kits of this invention can be performed by clinical laboratories, experimental laboratories, practitioners, or private individuals. Methods for fabricating the optical confinements and arrays of optical confinements are described in U.S. patent application Ser. Nos. 11/925,675, 11/925,650, 11/925,607, 11/626,610, 11/229,376, 11/228,925, 11/228,376 and 10/944,106, which are entirely incorporated herein by reference.

Asynchronous Sequencing Devices

An apparatus for sequencing a target nucleic acid molecule comprises one or more optical confinements for sequencing nucleic acid molecules, the one or more optical confinements comprising nucleic acid molecules having sequences similar or essentially similar to that of a target nucleic acid molecule. The apparatus further comprises a computer system configured to compile time sequences of incorporation of nucleotides or nucleotide analogs into nascent strands during asynchronous polymerization. In an embodiment of the invention, the nascent strands have different but overlapping sequences complementary to each of the nucleic acid molecules.

In embodiments of the invention, the time sequences of incorporation can be obtained by a computer system configured to receive information from an array having a plurality of optical confinements, wherein each optical confinement can have at most one nucleic acid molecule.

In embodiments of the invention, two or more nucleic acid molecules are provided in an array of optical confinements, wherein each optical confinement is configured to receive and transmit light. In an embodiment of the invention, an optical confinement comprises an effective observation volume that enables light to interact with a nucleic acid molecule. Sequencing information is obtained when the optical confinements are illuminated with light having a particular frequency (v).

Optical Confinements

Certain embodiments of the present invention provide the design of optical devices for characterizing molecules and/or monitoring chemical reactions. The optical devices of the present invention allow multiplexing of large numbers of single-molecule analyses in real-time under physiologically relevant conditions.

In one embodiment, the present invention provides a high-density array of optical confinements having a surface density exceeding $4 \times 10^4$ confinements per $mm^2$, or exceeding $1 \times 10^5$, wherein an individual confinement in the array provides an effective observation volume on the order of microliters, or nanoliters, or picoliters, or zeptoliters. The array may contain at least about $2 \times 10^5$, or at least about $1 \times 10^6$, or at least about $10 \times 10^7$ optical confinements. The individual confinements in the array can provide an effective observation volume less than about 1000 zeptoliters, or less than about 900 zeptoliters, or less than about 80 zeptoliters, or less than about 10 zeptoliters. In one embodiment, where desired, an effective observation volume less than 1 zeptoliter can be provided. In an embodiment of the invention, an individual confinement can yield an effective observation volume that permits resolution of individual molecules present at a physiologically-relevant concentration. The physiologically-relevant concentrations for most biochemical reactions can range from micromolar to millimolar because most of the enzymes have their Michaelis constants in these ranges. Accordingly, arrays of optical confinements can have an effective observation volume for detecting individual molecules present at a concentration greater than about 1 micromolar ($\mu M$), or greater than about 50 $\mu M$, or greater than about 100 $\mu M$.

To achieve the required observation volume for single-molecule analysis under physiologically relevant conditions, the array may comprise zero-mode waveguides (also "waveguide" or "guide" herein) or alternative nanoscale optical structures. Such alternative structures include, without limitation, porous films with reflective index media and confinements using index matching solids.

As used herein, "zero-mode waveguide" refers to an optical guide in which the majority of incident radiation is attenuated. In embodiments of the invention, more than 80%, or more than 90%, or more than 99% of the incident radiation can be attenuated. At such level of attenuation, no significant propagating modes of electromagnetic radiation exist in the guide. Consequently, the rapid decay of incident electromagnetic radiation at the entrance of such guide provides an extremely small observation volume that can be effective in detecting single molecules, even when they are present at a concentration as high as in the micromolar range.

The zero-mode waveguide of the present invention typically comprises a cladding surrounding a core (i.e., partially or fully), wherein the cladding is configured to preclude propagation of electromagnetic energy of a wavelength higher than the cutoff wavelength longitudinally through the core of the zero-mode waveguide. The cladding is typically made of materials that prevent any significant penetration of the electric and the magnetic fields of an electromagnetic radiation. Suitable materials for fabricating the cladding include, without limitation, alloys, metals, semiconductor-containing materials, and any combination thereof. Alloys include any of the numerous substances having metallic properties but comprising two or more elements of which at least one is a metal. Alloys may vary in the content or the amount of the respective elements, whether metallic or non metallic. Preferred alloys improve some desirable characteristics of the material over a pure elemental material. Characteristics that can be improved through the use of mixtures of materials include chemical resistance, thermal conductivity, electrical conductivity, reflectivity, grain size, coefficient of thermal expansion, brittleness, temperature tolerance, conductivity, and/or reduced grain size of the cladding.

Alloys suitable for the present invention may involve mixtures where one component is present at fractions as low as about 0.0001%. In other instances, alloys with large fractions of more than one compound will be desirable. One embodiment of the zero-mode waveguide ("ZMW") uses aluminum as the cladding of the ZMW structure. As an example of how alloys can be beneficial to a ZMW structure, it is useful to consider different alloys of aluminum and how they would affect a ZMW. In the art of metallurgy, numerous materials can be alloyed with aluminum. Non-limiting examples of materials suitable to alloy with aluminum are antimony, arsenic, beryllium, bismuth, boron, cadmium, calcium, carbon, cerium, chromium, cobalt, copper, gallium, hydrogen, indium, iron, lead, lithium, magnesium, manganese, mercury, molybdenum, nickel, niobium, phosphorous, silicon, vanadium, zinc and others. By way of example of how the introduction of another element could beneficially impact the ZMW performance, the introduction of boron to aluminum is known to increase the conductivity of aluminum. An increase in conductivity of the metal film may improve the performance by decreasing the penetration depth thereby decreasing the observation volume. An alloy of aluminum can be more than about 0.0001% of a dopant, or more than about 0.005% of a dopant, or more than about 0.1% of a dopant.

In contrast, some materials are expected to decrease the performance of the ZMW structure, and in these instances it will be desirable to take measures to eliminate certain impurities. For example, in certain applications it may be desirable to decrease the amount of lead or arsenic if toxicity of the device is a concern. Accordingly, a metal film can comprise less than about 1% arsenic, or less than about 0.1% arsenic, or less than about 0.001% arsenic, or less than about 0.00001% arsenic. Additionally, a metal film can comprise less than about 1% lead, or less than about 0.1% lead, or less than about 0.01% lead, or less than about 0.001% lead, or less than about 0.00001% lead. In other applications where optical confinement performance is especially important, impurities that tend to reduce the conductivity, thereby worsening the optical properties of the confinement, are undesirable. For example, vanadium is known in the art of metallurgy to reduce the conductivity of aluminum. As such, a metal film can comprise less than about 0.1% vanadium, or less than about 0.01% vanadium, or less than about 0.001% vanadium.

Semiconductor-containing materials suitable for fabricating the cladding are generally opaque; they may include silicon, silicates, silicon nitride, silicon oxide, gallium phosphide, gallium arsenide, or any combination thereof.

The cladding of the subject zero-mode waveguide may be coated with materials to improve its surface quality. For instance, coating may enhance the durability of the cladding material. In addition, coating can be particularly desirable if the reactants contained in the core are prone to interact or adhere to the cladding material. A variety of appropriate coating materials are available in the art. Some of the materials may covalently adhere to the surface, others may attach to the surface via non-covalent interactions. Non-limiting examples of coating materials include aluminum oxide film, silanization reagent (such as dimethychlorosilane, dimethydichlorosilane, hexamethyldisilazane, or trimethylehlorosilane), polymaleimide, and siliconizing reagents, such as silicon oxide, Aquasil™, and Surfasil™. Further details of zero-mode waveguides can be found in U.S. patent application Ser. Nos. 11/925,675, 11/925,650, 11/925,607,11/626,610, 11/229,376, 11/228,925, 11/228,376 and 10/944,106, which are entirely incorporated herein by reference.

In certain embodiments, it may be advantageous to construct a confinement from metal compositions that are inhomogeneous combinations of more than one material. For example, for certain applications, it may be beneficial to provide a composition that comprises more than one layer, each layer having a different composition, or composition that varies within a layer. This can have beneficial effects on several aspects of the performance of the confinement, including but not limited to, the nature of the optical confinement, the structural strength and behavior of the device, the characteristics of the surface chemistry of the device or the like. In one embodiment the confinement comprises two layers in which one of the layers serves to enhance the adhesion of the second layer to a substrate. In another embodiment, the composition of the cladding film varies as a function of the axial position relative to the confinement, so as to provide different optical performance than would be obtained from a layer of uniform composition. In a particular version of this embodiment, the film comprises a composition that has a larger value of skin depth close to the surface of the substrate, and comprises a composition that has a smaller value of skin depth farther from the surface of the substrate, so that the nature of the confinement is to be more uniform in shape near the surface and then tapering off more quickly a larger distances away from the substrate. In another embodiment, the thicknesses of two different layers comprising the cladding of the confinement are chosen so that a specific optical condition is achieved at the substrate of the device, such as constructive or destructive interference.

The internal cavity (i.e., the core) surrounded by the cladding may adopt a convenient size, shape or volume so long as propagating modes of electromagnetic radiation in the guide is effectively prevented. The core typically has a lateral dimension less than a cutoff wavelength ("$\lambda c$"). For a circular guide of diameter 'd' and having a clad of perfect conductor, $\lambda c$ is approximately 1.7×d. The cross sectional area of the core may be circular, elliptical, oval, conical, rectangular, triangular, polyhedral, or in any other shape. The various shapes can have particular suitability for certain applications. For instance, elongated cross-sections can be useful to provide enhanced access to molecules with mechanical persistence or stiffness, such as DNA. Cross sections ranging from extended slots to ovals of various aspect ratio will significant increase the accessibility of the persistent molecule to the detection zone of the structure, without excessive compromise in the axial attenuation of radiation. Although uniform cross sectional area is preferred, the cross sectional area may vary at any given depth of the guide if desired. Preferred average cross sectional areas range from about 100 nm$^2$ to about 10,000 nm$^2$.

In an embodiment of the invention, the core is non-cylindrical. In one aspect of this embodiment, a non-cylindrical core comprises an opening on the upper surface and a base at the bottom surface that is entirely surrounded by the cladding, wherein the opening is narrower in lateral dimension than the base. This configuration significantly restricts the diffusion of reactants, and hence increases the average residence time in the observation volume. Such configuration is particularly useful for measuring the association rate constant (on-rate) of a chemical reaction. In another aspect, the core comprises an opening that is wider in lateral dimension than the base. Such configuration allows easier access to large molecules that impose a steric or entropic hindrance to entering the structure if the open end of the zero mode waveguide was as small as the base needed to be for optical performance reasons. Examples include the accessibility for long strand polyelectrolytes such as DNA molecules that are subject to entropic forces opposing entry into small openings.

The zero-mode waveguides embodied in the present invention have a relatively high fill fraction ratio, typically above 0.0001, preferably above 0.001, more preferably above 0.01, and even more preferably above 0.1. As used herein, "fill fraction" of a pattern refers to the ratio of the area occupied by the foreground of the pattern to the total area occupied by the pattern (foreground and background, together). The terms "fill fraction ratio" and "fill faction" are used interchangeably. In the context of zero-mode waveguide, the foreground is considered to be the area occupied by the core of the zero-mode waveguide, and the background is the area between the zero-mode waveguide (e.g., the aluminum film that forms the cladding in certain designs). The zero-mode waveguides with high fill fraction ratios are particularly useful for performing homogenous assays. The fill fraction can be calculated by summing the total areas of all of the zero-mode waveguides in the array and dividing by the total available area including both the zero-mode waveguides and the spaces between them. For example, if a zero-mode waveguide has a diameter of 50 nm, then the area of this zero-mode waveguide is one fourth of 7,850 square nanometers or 1962.5 nm2. If these zero-mode waveguides are in a square array separated by 100 nm, the total available area is 10,000 square nanometers for each zero-mode waveguide. Therefore, the array has a fill fraction of one fourth of 78% or 19.6%, which would provide nearly four orders of magnitude higher signal strength in a surface binding assay than a zero-mode waveguide having a fill fraction on the order of 0.01%.

The cutoff wavelength is the wavelength above which the waveguide is essentially incapable of propagating electromagnetic energy along the waveguide under the illumination geometry used. Given the geometry of the core, and the properties of the cladding material, as well as the wavelength of the incident electromagnetic radiation, one skilled in the art can readily derive the cutoff wavelength by solving the Maxwell's equations. See, e.g., John D. Jackson, CLASSICAL ELECTRODYNAMICS, second edition, John Willey and Sons. The choice of the incident wavelength will depend on the particular application in which the subject array is to be employed. In certain embodiments, the incident wavelength may be selected from a range of about 10 nm to about 1 mm. For detecting fluorescent signals, the incident wavelength can be selected from the range of about 380 nm to about 800 nm. Polarized (linearly or preferably circularly polarized) or unpolarized incident radiation can be employed to illuminate the array in order to create a desired observation volume.

In another embodiment, the present invention provides an alternative optical confinement, which is referred to as an external reflection confinement ("ERC"). In contrast to the conventional total internal reflection confinement ("IRC"), in an ERC the low index medium is the electromagnetic radiation carrier, and the high index (and opaque) medium is the reflector. As such, the roles of the refractive indices are reversed as compared to IRC. ERC generally requires a means of providing an analyte (i.e., the molecules under investigation) in the opaque phase.

IRC relies on reflection of an electromagnetic radiation incident on an interface between high index of refraction and low index of refraction. When light is incident above the critical angle of total internal reflection (which is known in the art), all of the incident electromagnetic radiation is reflected and none is transmitted into the low index phase. A thin region of evanescent radiation is established proximate the interface on the low index side. This radiation field is typically an exponentially decaying field with an attenuation length in the range from about 100 nm to about 200 nm. The attenuation length is a function of the angle of incidence and the indices of refraction of the two phases. If the low index phase is a solution containing an analyte, then the evanescent radiation can be used to probe the analyte in the solution with a high degree of surface sensitivity.

In ERC, the carrier of the propagating electromagnetic radiation is a transparent low index film, and the analyte-bearing medium is a high-index metallic opaque film. In this case, most of the radiation is reflected irrespective of the angle of incidence, and non-reflected light is rapidly attenuated according to the skin depth of the metal. Typically, a means is provided to convey the analyte within the metal phase. Theses means can take the form of a nanocapillary tube constructed within the metal layer. When sufficiently small, the presence of such a tube will have little effect on the distribution of energy in the two media, but can be amply large enough to convey biomolecules. To be small enough, any defects in the metal film must be small compared with the wavelength of the illumination. This can be achieved because of the large ratio between the wavelength of visible light, and the typical size of biomolecules of interest. While visible light has a wavelength typically between about 400 nm and about 750 nm, biomolecules of interest are generally in the vicinity of about 1 nm to about 30 nm in diameter. The attenuation of the radiation at the interface can be used to confine illumination to a very small region of the analyte. A small hole in an index matched (to water) film on a high index substrate could provide lateral confinement beyond what is possible with diffraction limited optics in the TIR context. This could give a 100 zeptoliter confinement. In this method, a version of total internal reflection confinement is used in which a solid material index-matched to the analyte solution is applied to the substrate surface and then perforated with nanoscale holes. When used in TIR mode, these structures will provide additional confinements above what can be obtained with TIR alone.

Other alternative confinements are index matching solids. As an illustrative example, such optical confinement can be fabricated starting with a high index transparent susbtrate such as sapphire, spin coat 200 nm of PMMA (polymethyl methacrylate) resist resin. Exposure to electron beam lithography will render isolated spots soluble according to the pattern applied. After development, the device will have nanoscale holes in the PMMA layer and are ready to be used in a TIR setup. Axial confinement is unaffected by the PMMA layer, as it has nearly the same index of refraction as the solution containing the analyte, but the solution is physically prevented from approaching near the surface except where the holes are situated, providing a degree of lateral confinement given by the diameter of the holes.

Optical Systems

In various embodiments, the optical confinements can be provided with an optical system capable of detecting and/or monitoring interactions between reactants at the single-molecule level. Such optical system achieves these functions by first generating and transmitting an incident wavelength to the reactants contained in the confinements, followed by collecting and analyzing the optical signals from the reactants. Such systems typically employ an optical train that directs signals from an array of confinements onto different locations of an array-based detector to simultaneously detect multiple different optical signals from each of multiple different confinements. In particular, the optical trains typically include optical gratings or wedge prisms to simultaneously direct and separate signals having differing spectral characteristics from each confinement in an array to different locations on an array based optical detector using, e.g., a CCD. By separately directing signals from each confinement to different locations on a detector, and additionally separating the component signals from each confinement to separate locations, one can simultaneously monitor multiple confinements and multiple signals from each confinement.

The optical system applicable for the present invention comprises at least two elements, namely an excitation source and a photon detector. The excitation source generates and transmits incident light used to optically excite the reactants contained in the optical confinement. Depending on the intended application, the source of the incident light can be a laser, laser diode, a light-emitting diode ("LED"), a ultra-violet light bulb, and/or a white light source. Where desired, more than one source can be employed simultaneously. The use of multiple sources is particularly desirable in applications that employ multiple different reagent compounds having differing excitation spectra, consequently allowing detection of more than one fluorescent signal to track the interactions of more than one or one type of molecules simultaneously. A wide variety of photon detectors are available in the art. Photon (optical) detectors include, without limitation, optical readers, high-efficiency photon detection systems, photodiodes (e.g., avalanche photo diodes, or "APD"), cameras, charge couple devices ("CCD"), electron-multiplying charge-coupled devices ("EMCCD"), intensified charge coupled device ("ICCD"), and confocal microscope equipped with any of the foregoing detectors. Where desired, the subject arrays of optical confinements can contain various alignment aides or keys to facilitate a proper spatial placement of the optical confinement and the excitation sources, the photon detectors, or the optical transmission element, as described below.

In various embodiments, an optical system may also include an optical transmission element whose function can be manifold. First, it can collect and/or direct incident light to the optical confinement containing the reactants. Second, it can transmit and/or direct the optical signals emitted from the reactants inside the optical confinement to a photon detector. Third, it may select and/or modify the optical properties of the incident light or the emitted light from the reactants. Illustrative examples of such element are diffraction gratings, arrayed waveguide gratings ("AWG"), optic fibers, optical switches, mirrors, lenses (including microlens and nanolens) and collimators. Other examples include optical attenuators, polarization filters (e.g., dichroic filters), wavelength filters (low-pass, band-pass, or high-pass filters), wave-plates, and delay lines. In some embodiments, the optical transmission element can be planar waveguides in optical communication with the arrayed optical confinements. For instance, a planar waveguides can be operatively coupled to an array of zero-mode waveguides to directly channel incident wavelengths to the respective cores of the zero-mode waveguides so as to minimize the loss of wave energy. The planar channel can be included as a detachable unit located at the base of array substrate, or it can be bonded to the substrate as an integral part of the array.

The optical transmission element suitable for use in the present invention encompasses a variety of optical devices that channel light from one location to another in either an altered or unaltered state. Non-limiting examples of such optical transmission devices include optical fibers, diffraction gratings, arrayed waveguide gratings ("AWG"), optical switches, mirrors, (e.g., dichroic mirrors), lenses (including microlens and nanolens), collimators, filters, prisms, and any other devices that guide the transmission of light through proper refractive indices and geometries.

In an embodiment of the invention, the optical confinement of the present invention is operatively coupled to a photon detector. For instance, the arrayed optical confinement is operatively coupled to a respective and separate photon detector. The confinement and the respective detector can be spatially aligned (e.g., a one-to-one mapping) to permit an efficient collection of optical signals from the waveguide. A particularly preferred setup comprises an array of zero-mode waveguides, wherein each of the individual waveguides is operatively coupled to a respective microlens or a nanolens, preferably spatially aligned to optimize the signal collection efficiency. Alternatively, a combination of an objective lens, a spectral filter set or prism for resolving signals of different wavelengths, and an imaging lens can be used in an optical train to direct optical signals from each confinement to an array detector, e.g., a CCD, and concurrently separate signals from each different confinement into multiple constituent signal elements, e.g., different wavelength spectra, that correspond to different reaction events occurring within each confinement. Exemplary optical setups are described in U.S. patent application Ser. Nos. 11/925,675, 11/925,650, 11/925, 607, 11/626,610, 11/229,376, 11/228,925, 11/228,376 and 10/944,106, which are entirely incorporated herein by reference.

Arrays of embodiments of the invention may comprise a single row or a plurality of rows of optical confinements on the surface of a substrate, where a plurality of lanes is provided. In embodiments of the invention, more than 2, or more than 10, or more than 100 can be provided. The subject array of optical confinements may align horizontally or diagonally along the x-axis or the y-axis of the substrate (in reference to a two-dimensional plane parallel to a surface of a substrate). The individual confinements can be arrayed in any format across or over the surface of the substrate, such as in rows and columns so as to form a grid, or to form a circular, elliptical, oval, conical, rectangular, triangular, or polyhedral pattern. In one embodiment, to minimize the nearest-neighbor distances between adjacent optical confinements, a hexagonal array is preferred.

The array of optical confinements may be incorporated into a structure that provides for ease of analysis, high throughput, or other advantages, such as in a microtiter plate and the like. Such setup is also referred to herein as an "array of arrays." For example, the subject arrays can be incorporated into another array, such as microtiter or multi-well plate wherein each micro well of the plate contains a subject array of optical confinements. Such multi-well plates can comprise multiple reaction vessels or wells, e.g., in a 48 well, 96 well, 384 well, or 1536 well format. In such cases, the wells are typically disposed on 18 mm, 9 mm, 4.5 mm, or 2.25 mm centers, respectively. Illustrative examples of arrays of arrays are described in U.S. patent application Ser. Nos. 11/925,675, 11/925,650, 11/925,607, 11/626,610, 11/229,376, 11/228, 925, 11/228,376 and 10/944,106, which are entirely incorporated herein by reference.

EXAMPLES

Example 1

A target circular DNA molecule is replicated into a plurality of nucleic acid molecules having substantially similar nucleotide sequences. The nucleic acid molecules are distributed to an array of optical confinements, wherein each optical confinement has at most one nucleic acid molecule. Next, substantially similar primers are provided. The primers form complexes with the nucleic acid molecules at substantially similar locations. Next, polymerization enzymes are provided. The polymerization enzymes form complexes with the nucleic acid molecules at locations in which the primers are complexed with the nucleic acid molecules. A reagent of nucleotide analogs is provided to begin polymerization reactions in each of the optical confinements. The reactions are permitted to run for approximately 10 minutes prior to illuminating the optical confinement with light. Upon illumination, a computer system electrically connected to a detector collects sequence information related to polymerization reactions in the optical confinements. Different but overlapping nascent strand sequence information is collected by the computer system. A software algorithm aligns the sequence information at points of overlap to yield an overall sequence of the target DNA molecule. Redundant sequence data is used to account for sequencing errors (e.g., due to misincorporation of a particular nucleotide).

Although described in some detail for purposes of illustration, it will be readily appreciated that a number of variations known or appreciated by those of skill in the art may be practiced within the scope of present invention. To the extent not already expressly incorporated herein, all published references and patent documents referred to in this disclosure are incorporated herein by reference in their entirety and for all purposes.

Example 2

In an exemplary embodiment, a method for sequencing a target nucleic acid molecule comprises providing two or more nucleic acid molecules (also "plurality of nucleic acid molecules" herein) having the same or essentially the same sequences as the target nucleic acid molecule. Each of the two or more nucleic acid molecules is complexed with (or brought in association with) a primer and a polymerase. In one embodiment, individual polymerases are complexed at different locations of the target nucleic acid molecule. In another embodiment, individual polymerases are complexed at the same or essentially the same location of the target nucleic acid molecule.

Next, the two or more nucleic acid molecules are subjected to polymerization reactions, whereby nucleotides or nucleotide analogs are paired with complementary nucleotides on each of the two or more nucleic acid molecules to form two or more nascent strands, wherein each nascent strand is complementary to a nucleic acid molecule undergoing polymerization. During at least a portion of the polymerization reactions, time sequences of incorporation of nucleotides or nucleotide analogs are obtained. In one embodiment, time sequences of incorporation of nucleotides or nucleotide analogs are obtained when the two or more nucleic acid molecules are illuminated. The time sequences of incorporation are compiled to form a sequence of the target nucleic acid molecule. In embodiments of the invention, the time sequences of incorporation are compiled using a computer system configured to collect sequence information. In embodiments of the invention, the time sequences of incorporation of nucleotides or nucleotide analogs represent segments of the target nucleic acid sequence. In one embodiment, the time sequences of incorporation of nucleotides or nucleotide analogs represent different but overlapping segments of the target nucleic acid sequence.

Example 3

FIG. 2A and FIG. 2B illustrate an asynchronous polymerization reaction established by utilizing different rates of polymerization between polymerases. FIG. 2A shows a first nucleic acid molecule 110, a second nucleic acid molecule 120 and a third nucleic acid molecule 130. In embodiments of the invention, the nucleic acid molecules 110, 120 and 130 are each disposed in separate optical confinements (not shown). In the illustrated embodiment, the nucleic acid molecules 110, 120 and 130 have the same or essentially the same sequences as a target nucleic acid molecule. The nucleic acid molecules 110, 120 and 130, as illustrated, are circular (e.g., cDNA). However, the nucleic acid molecules 110, 120 and 130 can be linear. Further, the nucleic acid molecules can be bound to a support surface, such as a bottom surface of an optical confinement.

With continued reference to FIG. 2A, at time '0', the first nucleic acid molecule 10 is complexed with a first primer 112 and a first polymerization enzyme 114; the second nucleic acid molecule 120 is complexed with a second primer 122 and a second polymerization enzyme 124; and the third nucleic acid molecule 130 is complexed with a third primer 132 and a third polymerization enzyme 134. In the illustrated embodiment, the first primer 112, the second primer 122 and the third primer 132 have substantially similar sequences. Next, nucleotide or nucleotide analogs are provided in the optical confinements to begin the polymerization reactions.

FIG. 2B shows the nucleic acid molecules 110, 120 and 130 after a time 'n' has elapsed following commencement of the polymerization reactions. During the polymerization reactions, a first nascent strand 144 complementary to a portion of the first nucleic acid molecule 110 is formed; a second nascent strand 154 complementary to a portion of the second nucleic acid molecule 120 is formed; and a third nascent strand 164 complementary to a portion of the third nucleic acid molecule 130 is formed. In the illustrated embodiment, the first polymerization enzyme 114 polymerizes at a lower rate (e.g. by stochastic considerations, enzyme subspecies, varied mico-environments, etc.) than the second polymerization enzyme 124, and the second polymerization enzyme polymerizes at a lower rate than the third polymerization enzyme 134. Accordingly, at time 'n' the polymerization enzymes are at different locations of the nucleic acid molecules 110, 120 and 130; the polymerization enzymes 114, 124 and 134 are polymerizing asynchronously with respect to one another. The optical confinements comprising the nucleic acid molecules 110, 120 and 130 are illuminated (hv). The light can then be transmitted to one or more optical detectors (not shown), and sequence information can be compiled by a computer system (not shown).

Example 4

Figure 3:
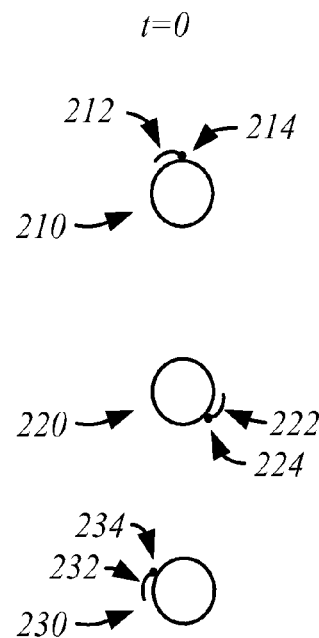
FIG. 3 schematically illustrates a method for establishing asynchronous polymerization between three polymerization enzymes.

FIG. 3 shows an illustration of an asynchronous polymerization reaction established by localizing polymerases at different locations on template nucleic acids. FIG. 3 shows a first nucleic acid molecule 210, a second nucleic acid molecule 220, and a third nucleic acid molecule 230. The first nucleic acid molecule 210 is complexed with a first primer 212 and a first polymerase 214; the second nucleic acid molecule 220 is complexed with a second primer 222 and a second polymerase 223; and the third nucleic acid molecule 230 is complexed with a third primer 232 and a third polymerase. In the illustrated embodiment, the first primer 212, the second primer 222 and the third primer 232 have different sequences. Accordingly, they form complexes with different portions of the nucleic acid molecules 210, 220 and 230.

With continued reference to FIG. 3, at time '0', polymerization reactions may be commenced by introducing nucleotides or nucleotide analogs into the optical confinements having the nucleic acid molecules 210, 220 and 230. In the illustrated embodiment, the polymerization enzymes 214, 224 and 234 would be polymerizing asynchronously with respect to one another because the polymerization reactions commence at different portions of the nucleic acid molecules 210, 220 and 230. Sequencing may begin by illuminating the optical confinements with light. Reflected light may be collected with one or more optical detectors (not shown), and a computer system (not shown) can be used to compile sequence data.

Example 5

In aspects of the invention, obtaining sequence information for a target (or template) nucleic acid molecule comprises providing a polymerization environment; providing a primers, nucleic acid molecules and polymerization enzymes in an optical confinements; providing nucleotides or nucleotide analogs in the optical confinements to commence polymerization of strands complementary to the nucleic acid molecules; establishing asynchronous polymerization reactions; and obtaining sequence information using an optical detection system.

It should be understood from the foregoing that, while particular embodiments have been illustrated and described, various modifications can be made thereto and are contemplated herein. It is also not intended that the invention be limited by the specific examples provided within the specification. While the invention has been described with reference to the aforementioned specification, the descriptions and illustrations of embodiments of the invention herein are not meant to be construed in a limiting sense. Furthermore, it shall be understood that all aspects of the invention are not limited to the specific depictions, configurations or relative proportions set forth herein which depend upon a variety of conditions and variables. Various modifications in form and detail of the embodiments of the invention will be apparent to a person skilled in the art. It is therefore contemplated that the invention shall also cover any such modifications, variations and equivalents.

What is claimed is:

1. A method for sequencing a target nucleic acid molecule, the method comprising:
    (a) providing a first nucleic acid molecule and a second nucleic acid molecule, the first nucleic acid molecule and the second nucleic acid molecule comprising the same sequence as the target nucleic acid molecule, wherein the first nucleic acid molecule is complexed with a first primer and a first polymerase and the second nucleic acid molecule is complexed with a second primer and a second polymerase, wherein the first polymerase has a different rate of polymerization from the second polymerase, and further wherein the first nucleic acid molecule is a first circular template and the second nucleic acid molecule is a second circular template;
    (b) subjecting the first circular template to a first polymerization reaction to yield a first strand complementary to the first nucleic acid molecule;
    (c) subjecting the second circular template to a second polymerization reaction to yield a second strand complementary to the second nucleic acid molecule, wherein the first polymerization reaction is asynchronous compared to the second polymerization reaction, the asynchronous due to different rates of polymerization exhibited by the first polymerase on the first circular template and the second polymerase on the second circular template;
    (d) obtaining overlapping time sequences of incorporation of nucleotides or nucleotide analogs into the first strand and the second strand during the asynchronous polymerization reactions; and
    (e) sequencing the target nucleic acid molecule by compiling, using a programmed computer, the overlapping time sequences of incorporation of nucleotides into the first and second strands obtained during the asynchronous polymerization reactions.

2. The method of claim 1, wherein each of the first strand and second strand shares sequence identity to a contiguous segment of the target nucleic acid molecule having a length that is no more than about 95% of the entire length of the target nucleic acid molecule.

3. The method of claim 1, wherein each of the first strand and second strand shares sequence identity to a contiguous segment of the target nucleic acid molecule having a length that is no more than about 75% of the entire length of the target nucleic acid molecule.

4. The method of claim 1, wherein each of the first strand and second strand shares sequence identity to a contiguous segment of the target nucleic acid molecule having a length that is no more than about 50% of the entire length of the target nucleic acid molecule.

5. The method of claim 1, wherein the first primer and the second primer have the same sequence of nucleotides or nucleotide analogs.

6. The method of claim 1, wherein the first primer and the second primer have different sequences of nucleotides or nucleotide analogs.

7. The method of claim 1, wherein the first circular template and the second circular template are attached to a support surface.

8. The method of claim 1, wherein the first polymerase and the second polymerase are DNA polymerases.

9. The method of claim 1, wherein the first polymerase and the second polymerase are polymerases exhibiting strand-displacement activity.

10. The method of claim 1, wherein the target nucleic acid molecule is selected from deoxyribonucleic acid, ribonucleic acid, locked nucleic acid, glycol nucleic acid and threose nucleic acid.

11. The method of claim 1, wherein the overlapping time sequences of incorporation of nucleotides or nucleotide analogs into the first strand and the second strand represent segments of the target nucleic acid sequence.

12. The method of claim 1, wherein the first strand and the second strand overlap by about 5 or more nucleotides.

13. The method of claim 1, wherein the first strand and the second strand overlap by about 10 or more nucleotides.

14. The method of claim 1, wherein the first strand and the second strand overlap by about 20 or more nucleotides.

15. A method for sequencing a target nucleic acid molecule, the method comprising:
    (a) providing two or more circular nucleic acid molecules comprising the same sequences as the target nucleic acid molecule, wherein each of the two or more circular nucleic acid molecules is complexed with a primer and a polymerase, wherein individual polymerases are complexed at different locations on the circular nucleic acid molecules such that at least two nascent strands of different but overlapping sequences are achieved;
    (b) subjecting the two or more circular nucleic acid molecules to polymerization reactions to yield the at least two nascent strands, wherein the polymerization reactions are asynchronous polymerization reactions due to the different locations of the individual polymerases on the circular nucleic acid molecules;

(c) obtaining overlapping time sequences of incorporation of nucleotides or nucleotide analogs into the nascent strands of different but overlapping sequences during the asynchronous polymerization reactions; and (d) aligning and compiling the overlapping time sequences of incorporation obtained during the asynchronous polymerization reactions, thereby sequencing the target nucleic acid molecule.

16. The method of claim 1, wherein the first polymerase and the second polymerase are attached to a support surface.

* * * * *